US009321759B2

(12) United States Patent
Greene et al.

(10) Patent No.: US 9,321,759 B2
(45) Date of Patent: Apr. 26, 2016

(54) METHODS AND USE OF BIFUNCTIONAL ENZYME-BUILDING CLAMP-SHAPED MOLECULES

(75) Inventors: Mark I. Greene, Penn Valley, PA (US); Hongtao Zhang, Paoli, PA (US); Alan Berezov, West Hollywood, CA (US); Zheng Cai, Wynnewood, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 54 days.

(21) Appl. No.: 14/005,066

(22) PCT Filed: Mar. 16, 2012

(86) PCT No.: PCT/US2012/029410
§ 371 (c)(1),
(2), (4) Date: Dec. 23, 2013

(87) PCT Pub. No.: WO2012/125913
PCT Pub. Date: Sep. 20, 2012

(65) Prior Publication Data
US 2014/0309246 A1   Oct. 16, 2014

Related U.S. Application Data

(60) Provisional application No. 61/453,682, filed on Mar. 17, 2011, provisional application No. 61/486,453, filed on May 16, 2011.

(51) Int. Cl.
*C07D 417/12* (2006.01)
*A61K 31/497* (2006.01)
*A61K 31/517* (2006.01)
*C07D 239/94* (2006.01)
*C07D 285/125* (2006.01)

(52) U.S. Cl.
CPC ............ *C07D 417/12* (2013.01); *A61K 31/497* (2013.01); *A61K 31/517* (2013.01); *C07D 239/94* (2013.01); *C07D 285/125* (2013.01)

(58) Field of Classification Search
CPC ........................... C07D 417/12; A61K 31/517
USPC ....................................... 514/266.2; 544/284
See application file for complete search history.

(56) References Cited

U.S. PATENT DOCUMENTS

| | | | |
|---|---|---|---|
| 5,457,105 | A | 10/1995 | Barker |
| 5,616,582 | A | 4/1997 | Barker |
| 5,747,498 | A | 5/1998 | Schnur et al. |
| 5,770,599 | A | 6/1998 | Gibson |
| 6,251,912 | B1 | 6/2001 | Wissner et al. |
| 6,391,874 | B1 | 5/2002 | Cockerill et al. |
| 6,713,485 | B2 | 3/2004 | Carter |
| 6,727,256 | B1 | 4/2004 | Carter et al. |
| 6,828,320 | B2 | 12/2004 | Cockerill et al. |
| 6,900,221 | B1 | 5/2005 | Norris |
| 7,087,613 | B2 | 8/2006 | Raggon et al. |
| 7,157,466 | B2 | 1/2007 | McClure et al. |
| 7,547,781 | B2 | 6/2009 | Qian et al. |
| 7,585,859 | B2 | 9/2009 | Ibrahim et al. |
| RE41,065 | E | 12/2009 | Schnur |
| 7,846,938 | B2 | 12/2010 | Cai et al. |
| 2005/0084905 | A1 | 4/2005 | Prescott et al. |
| 2007/0123537 | A1 | 5/2007 | Herget |
| 2008/0004297 | A1 | 1/2008 | Cai et al. |
| 2008/0139590 | A1 | 6/2008 | Qian et al. |
| 2008/0194578 | A1 | 8/2008 | Qian et al. |
| 2008/0221132 | A1 | 9/2008 | Cai et al. |
| 2009/0076022 | A1 | 3/2009 | Cai et al. |
| 2009/0111772 | A1 | 4/2009 | Cai et al. |
| 2009/0209758 | A1 | 8/2009 | Qian et al. |
| 2009/0306101 | A1 | 12/2009 | Solca et al. |
| 2009/0318480 | A1 | 12/2009 | Solca |

FOREIGN PATENT DOCUMENTS

| | | |
|---|---|---|
| EP | 0068553 | 1/1983 |
| WO | WO 2012/125904 A1 | 9/2012 |
| WO | WO 2012/125913 A1 | 9/2012 |

OTHER PUBLICATIONS

Pinedo et al. (2000).*
McMahon et al (2000).*
Chandregowda, et al, "Synthesis and in Vitro Antitumor Activities of Novel 4-Anilinoquinazoline Derivatives", European Journal of Medicinal Chemistry, Editions Scientifique Elsevier, Paris, FR, Jul. 1, 2009, 44(7), 3046-3055.
Hatti et al, In-Silico Interaction Studies of Quinazoline Derivatives for their Inhibitory Action on Both Wild and Mutant EGfRs, Journal of Proteomics & Bioinformatics, Mar. 12, 2009, 2(3), pp. 126-130, http://www.omicsonline.cqm1ArchiveJPB/2009/Mar/01/.
Noolvi et al, "3D Qsar Studies on a Series of Quinazoline Derrivatives as Tyrosine Kinase (EGFR) Inhibitor: The K-Nearest Neighbor Molecular Field Analysis Approach", Journal of Basic and Clinical Pharmacy, Jun. 1, 2010, 1(3), pp. 153-175.
Berge, "Pharmaceutical Salts", Journal of Pharmaceutical Sciences, Jan. 1977, 66(1):1-19.
Choi et al, "EGF-Independent Activation of Cell-Surface Egf Receptors Harboring Mutations Found in Gefitinib-Sensitive Lung Cancer", Oncogene, 2007, 26, 1567-1576.
Ewing, "DOCK 4.0: Search Strategies for Automated Molecular Docking of Flexible Molecule databases", Journal of Computer-Aided Molecular Design, 2001, 15: 411-428.
Fabian et al, "A Small Molecule-Kinase Interaction Map for Clinical Kinase Inhibitors", Nature Biotechnology, Mar. 2005, 23(3), 329-336.

(Continued)

*Primary Examiner* — Paul V Ward
(74) *Attorney, Agent, or Firm* — Baker & Hostetler LLP

(57) ABSTRACT

This invention is in the fields of cancer therapy. More particularly it concerns compounds which are useful agents for inhibiting cell proliferative disorders, especially those disorders characterized by over activity and/or inappropriate activity of a EGFR, including EGFR-related cancers, and methods for treating these disorders.

35 Claims, 11 Drawing Sheets

(56) References Cited

OTHER PUBLICATIONS

Fingl et al, "The Pharmacological Basis of Therapeutics", Fourth Edition, 1975, 1(1), The Macmillan Company, New York, NY 10022, 6 pages.

Heymann et al, "The T790M "Gatekeeper" Mutation in EGFR Mediates Resistance to Low Concentrations of an Irreversible EGFR Inhibitor", Mol. Cancer Ther., Apr. 2008;7:874-879.

International Patent Application No. PCT/US12/29386: International Search Report and the Written Opinion dated Jun. 29, 2012, 10 pages.

International Patent Appln. No. PCT/US2012/029410: International Preliminary Report dated Sep. 26, 2013, 7 pages.

International Patent Appln. No. PCT/US2012/029410: International Search Report and the Written Opinion dated Jul. 5, 2012, 11 pages.

Jackman, "Impact of Epidermal Growth Factor Receptor and KRAS Mutations on Clinical Outcomes in Previously Untreated Non-Small Cell Lung Cancer Patients: Results of an Online Tumor Registry of Clinical Trials", Clinical Cancer Research, Aug. 2009, 15(16):5267-5273.

Kotra et al, "Homology Models of the Mutated EGFR and Their Response Towards Quinazolin Analogues", Journal of Molecular Graphics and Modelling, 2008, 27, 244-254.

Kwak et al, "Irreversible Inhibitors of the EGF Receptor May Circumvent Acquired resistance to Gefitinib", PNAS, May 24, 2005, 102(21), 7665-7670.

Lynch et al, "Activating Mutations in the Edpidermal Growth Factor Receptor Underlying Responsiveness of Non-Small Cell Lung Cancer to Gefitinib", N. Engl. J. Med., May 2004, 350, 2129-2139.

Minna et al, "A Bull's Eye for Targeted Lung Cancer Therapy", Science, Jun. 4, 2004, 304, 1458-1461.

Paez et al, "EGFR Mutations in Lung Cancer: Correlation with Clinical Response to Gefitinib Therapy", Science, Jun. 4, 2004, 304, 1497-1500.

Sordella, "Gefitinib-Sensitizing EGFR Mutations in Lung Cancer Activate Anti-Apoptotic Pathways", Science, Aug. 20, 2004, 1163-1167.

Vikis et al, "EGFR-T790M is a Rare Ling Cancer Susceptibility Allele with Enhanced Kinase Activity", Cancer Research, May 2007, 67:4665-4670.

Wakeling et al, "Specific Inhibition of Epidermal Growth Factor Receptor Tyrosine Kinase by 4-anilinoquinazolines", Breast Cancer Research and Treatment, 1996, 38:67-73.

Yu et al, "Resistance to an Irreversible Epidermal Growth Factor Receptor (EGFR) Inhibitor in EGFR-Mutant Lung Cancer Reveals Novel Treatment Strategies", Cancer Research, Nov. 1, 2007, 67:10417-10427.

Yun et al, "Structures of Lung Cancer-Derived EGFR Mutants and Inhibitor Complexes: Mechanism of Activation and Insights Into Differential Inhibitor Sensitivity", Cancer Cell., Mar. 2007; 11(3): 217-227.

Boland, E.W., "Hydrocortisone Administered Orally in Rheumatoid Arthritis", Annals of the Rheumatic Diseases, Jun. 1953, 12(2), 125-128.

Ranson et al, "A Phase I Dose-Escalation and Bioavailability Study of Oral and Intravenous formulations of Erlotinib (Tarceva®, OSI-774) in Patients with Advanced Solid Tumors of Epithelial Origin", Cancer Chemotherapy Pharmacology, May 2010, 66(1), 53-58.

* cited by examiner

FIG. 1
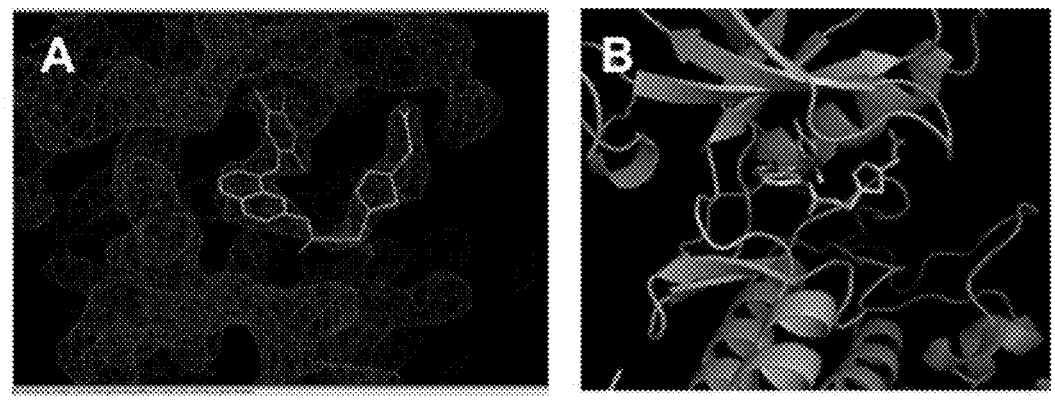
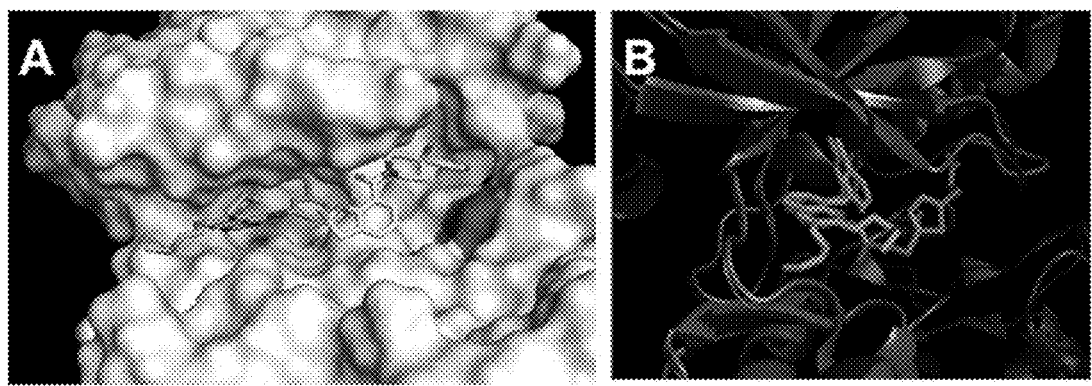

FIG. 4
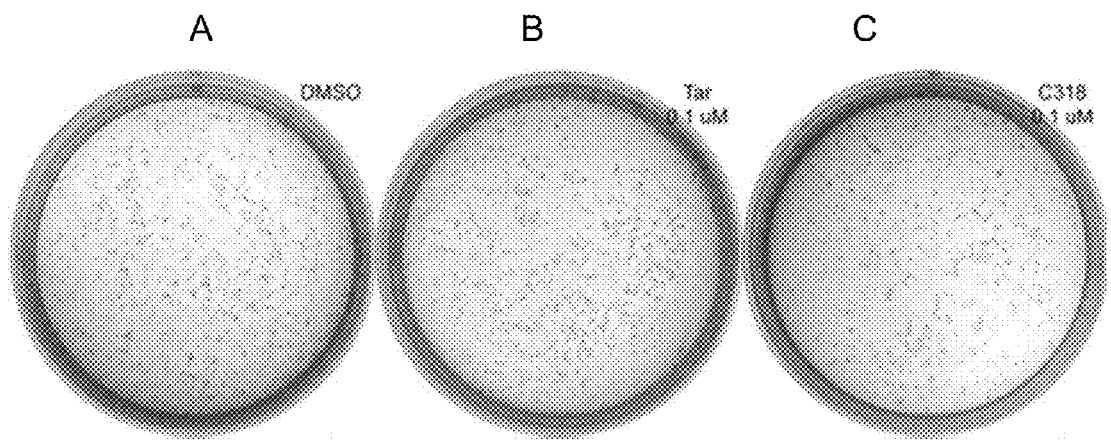
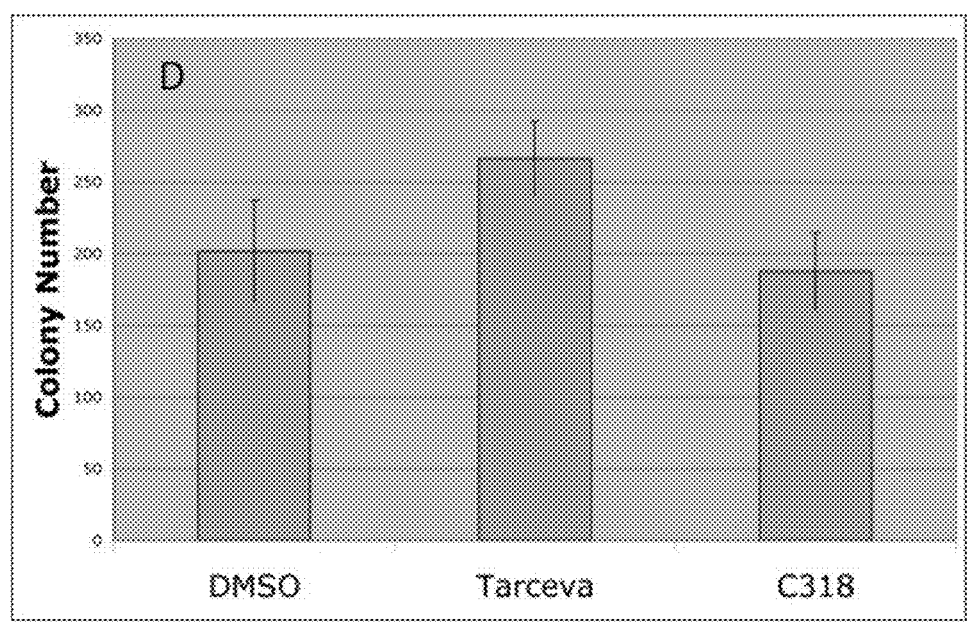

FIG. 5

Human EGFR Kinase domain

```
                                                       AGT GGA GAA GCT CCC AAC
                                                       ser gly glu ala pro asn
2347/701                                       2377/711
CAA GCT CTC TTG AGG ATC TTG AAG GAA ACT        GAA TTC AAA AAG ATC AAA GTG CTG GGC TCC
gln ala leu leu arg ile leu lys glu thr        glu phe lys lys ile lys val leu gly ser
2407/721                                       2437/731
GGT GCG TTC GGC ACG GTG TAT AAG GGA CTC        TGG ATC CCA GAA GGT GAG AAA GTT AAA ATT
gly ala phe gly thr val tyr lys gly leu        trp ile pro glu gly glu lys val lys ile
2467/741                                       2497/751
CCC GTC GCT ATC AAG GAA TTA AGA GAA GCA        ACA TCT CCG AAA GCC AAC AAG GAA ATC CTC
pro val ala ile lys glu leu arg glu ala        thr ser pro lys ala asn lys glu ile leu
2527/761                                       2557/771
GAT GAA GCC TAC GTG ATG GCC AGC GTG GAC        AAC CCC CAC GTG TGC CGC CTG CTG GGC ATC
asp glu ala tyr val met ala ser val asp        asn pro his val cys arg leu leu gly ile
2587/781                                       2617/791
TGC CTC ACC TCC ACC GTG CAG CTC ATC ACG        CAG CTC ATG CCC TTC GGC TGC CTC CTG GAC
cys leu thr ser thr val gln leu ile thr        gln leu met pro phe gly cys leu leu asp
2647/801                                       2677/811
TAT GTC CGG GAA CAC AAA GAC AAT ATT GGC        TCC CAG TAC CTG CTC AAC TGG TGT GTG CAG
tyr val arg glu his lys asp asn ile gly        ser gln tyr leu leu asn trp cys val gln
2707/821                                       2737/831
ATC GCA AAG GGC ATG AAC TAC TTG GAG GAC        CGT CGC TTG GTG CAC CGC GAC CTG GCA GCC
ile ala lys gly met asn tyr leu glu asp        arg arg leu val his arg asp leu ala ala
2767/841                                       2797/851
AGG AAC GTA CTG GTG AAA ACA CCG CAG CAT        GTC AAG ATC ACA GAT TTT GGG CTG GCC AAA
arg asn val leu val lys thr pro gln his        val lys ile thr asp phe gly leu ala lys
2827/861                                       2857/871
CTG CTG GGT GCG GAA GAG AAA GAA TAC CAT        GCA GAA GGA GGC AAA GTG CCT ATC AAG TGG
leu leu gly ala glu glu lys glu tyr his        ala glu gly gly lys val pro ile lys trp
2887/881                                       2917/891
ATG GCA TTG GAA TCA ATT TTA CAC AGA ATC        TAT ACC CAC CAG AGT GAT GTC TGG AGC TAC
met ala leu glu ser ile leu his arg ile        tyr thr his gln ser asp val trp ser tyr
2947/901                                       2977/911
GGG GTG ACC GTT TGG GAG TTG ATG ACC TTT        GGA TCC AAG CCA TAT GAC GGA ATC CCT GCC
gly val thr val trp glu leu met thr phe        gly ser lys pro tyr asp gly ile pro ala
3007/921                                       3037/931
AGC GAG ATC TCC TCC ATC CTG GAG AAA GGA        GAA CGC CTC CCT CAG CCA CCC ATA TGT ACC
ser glu ile ser ser ile leu glu lys gly        glu arg leu pro gln pro pro ile cys thr
3067/941                                       3097/951
ATC GAT GTC TAC ATG ATC ATG GTC AAG TGC        TGG ATG ATA GAC GCA GAT AGT CGC CCA AAG
ile asp val tyr met ile met val lys cys        trp met ile asp ala asp ser arg pro lys
3127/961                                       3157/971
TTC CGT GAG TTG ATC ATC GAA TTC TCC AAA        ATG GCC CGA GAC CCC CAG CGC TAC CTT GTC
phe arg glu leu ile ile glu phe ser lys        met ala arg asp pro gln arg tyr leu val
3187/981                                       3217/991
ATT CAG GGG GAT GAA AGA ATG CAT TTG CCA        AGT CCT ACA GAC TCC AAC TTC TAC CGT GCC
ile gln gly asp glu arg met his leu pro        ser pro thr asp ser asn phe tyr arg ala
3247/1001                                      3277/1011
CTG ATG GAT GAA GAA GAC ATG GAC GAC GTG        GTG GAT GCC GAC GAG TAC CTC ATC CCA CAG
leu met asp glu glu asp met asp asp val        val asp ala asp glu tyr leu ile pro gln
3307/1021                                      3337/1031
CAG GGC
gln gly
```

C53: MW=713

FIG. 6, cont'd
C318: MW=629
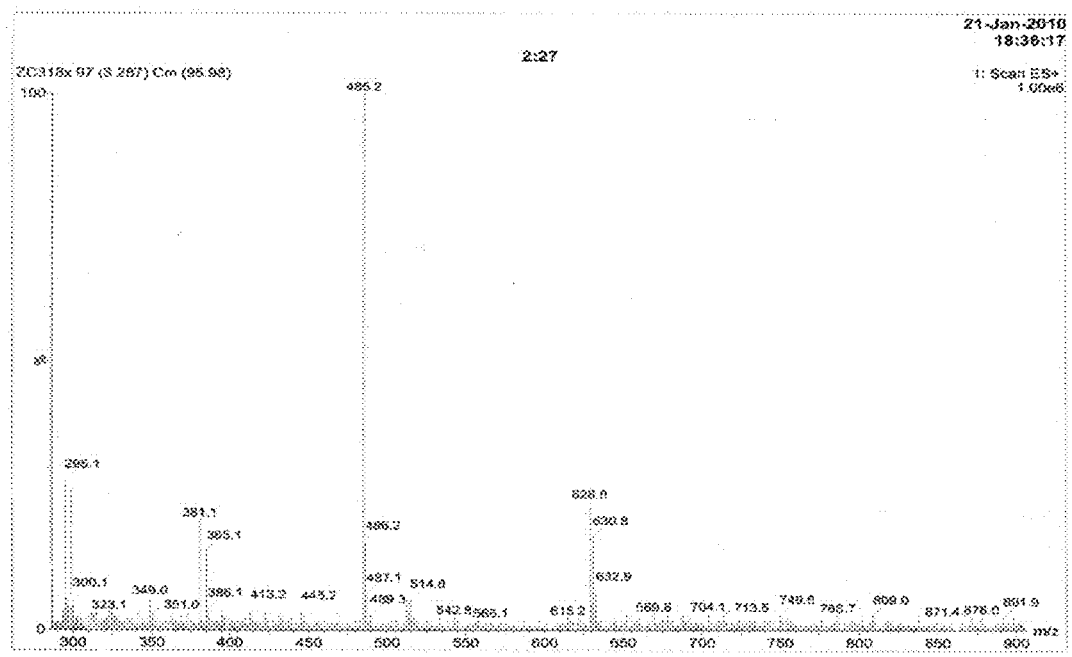

FIG. 6, cont'd
C318A: MW=584
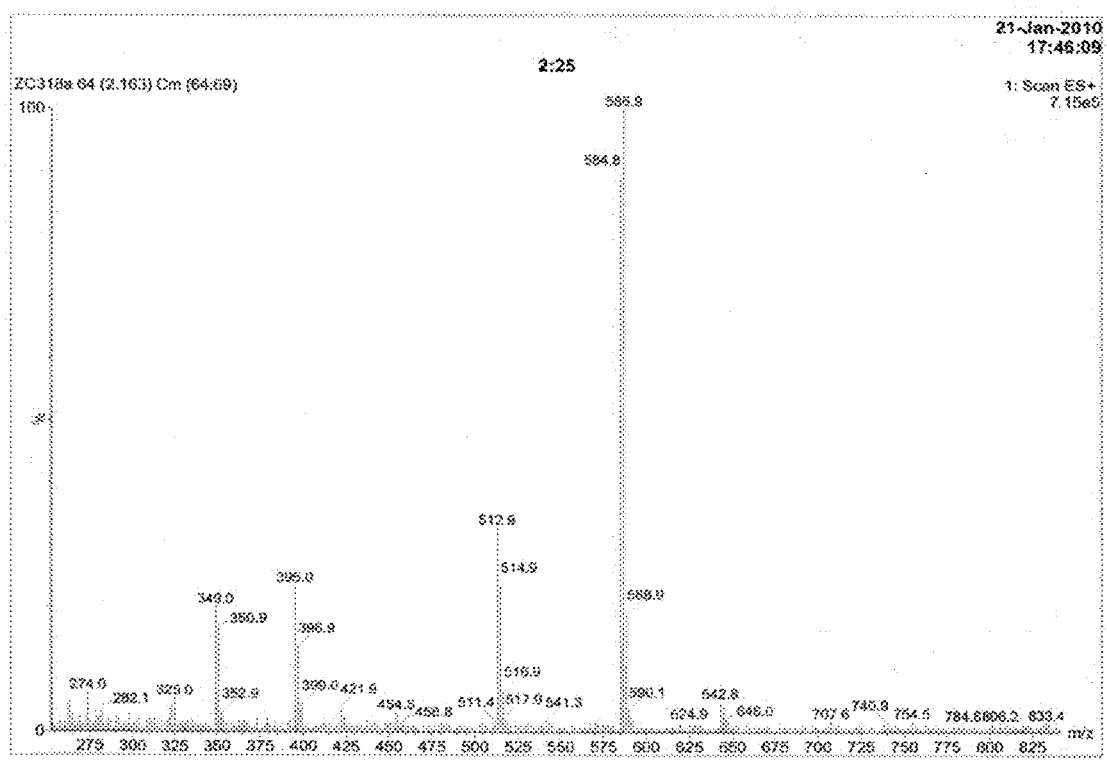

FIG. 6, cont'd
C318D: MW=599
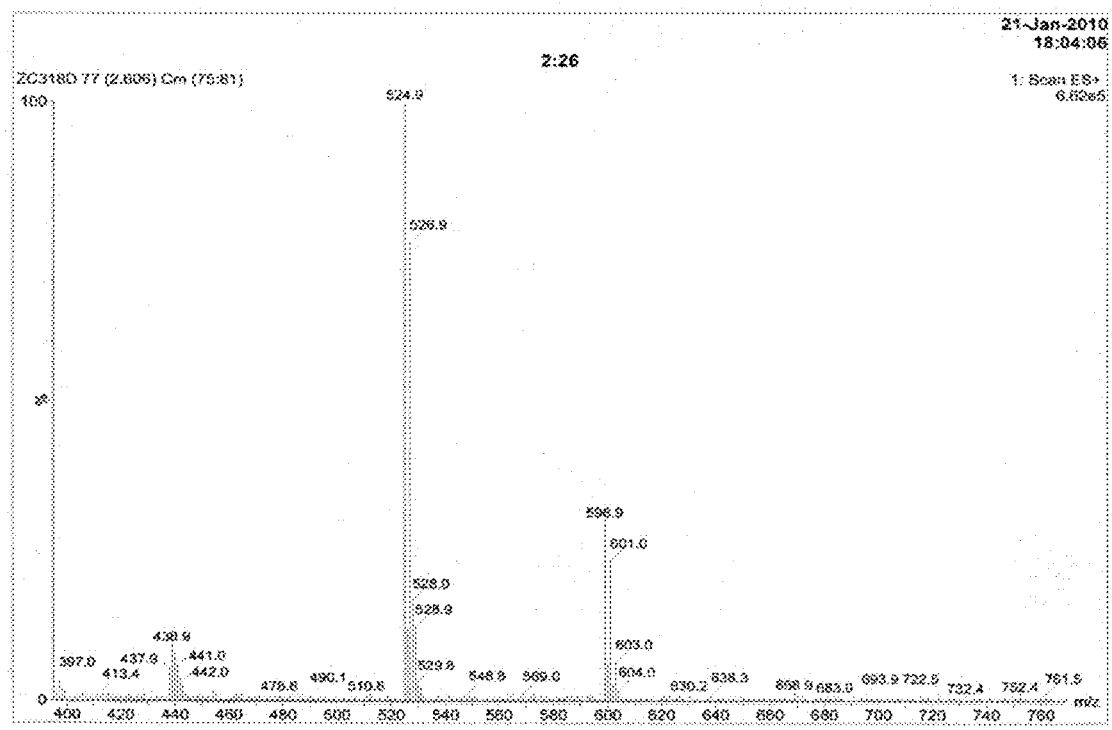

FIG. 6, cont'd
C318F: MW=567
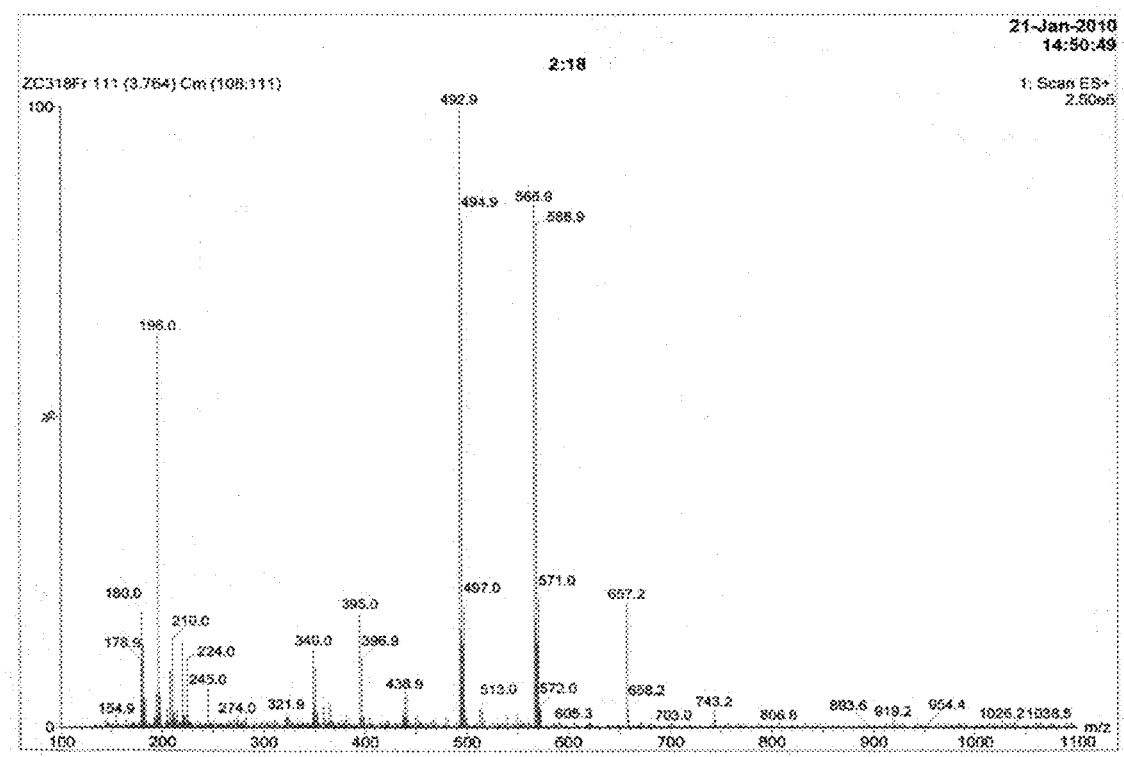

SEQUENCE LISTING

```
<160> NUMBER OF SEQ ID NOS: 2

<210> SEQ ID NO 1
<211> LENGTH: 984
<212> TYPE: DNA
<213> ORGANISM: Homo sapiens
<220> FEATURE:
<221> NAME/KEY: CDS
<222> LOCATION: (1)..(984)

<400> SEQUENCE: 1 agt gga gaa gct ccc aac caa gct ctc ttg agg atc ttg aag gaa act       48
Ser Gly Glu Ala Pro Asn Gln Ala Leu Leu Arg Ile Leu Lys Glu Thr
1               5                   10                  15 gaa ttc aaa aag atc aaa gtg ctg ggc tcc ggt gcg ttc ggc acg gtg       96
Glu Phe Lys Lys Ile Lys Val Leu Gly Ser Gly Ala Phe Gly Thr Val
                20                  25                  30 tat aag gga ctc tgg atc cca gaa ggt gag aaa gtt aaa att ccc gtc      144
Tyr Lys Gly Leu Trp Ile Pro Glu Gly Glu Lys Val Lys Ile Pro Val
            35                  40                  45 gct atc aag gaa tta aga gaa gca aca tct ccg aaa gcc aac aag gaa      192
Ala Ile Lys Glu Leu Arg Glu Ala Thr Ser Pro Lys Ala Asn Lys Glu
        50                  55                  60 atc ctc gat gaa gcc tac gtg atg gcc agc gtg gac aac ccc cac gtg      240
Ile Leu Asp Glu Ala Tyr Val Met Ala Ser Val Asp Asn Pro His Val
65                  70                  75                  80 tgc cgc ctg ctg ggc atc tgc ctc acc tcc acc gtg cag ctc atc acg      288
Cys Arg Leu Leu Gly Ile Cys Leu Thr Ser Thr Val Gln Leu Ile Thr
                85                  90                  95 cag ctc atg ccc ttc ggc tgc ctc ctg gac tat gtc cgg gaa cac aaa      336
Gln Leu Met Pro Phe Gly Cys Leu Leu Asp Tyr Val Arg Glu His Lys
                100                 105                 110 gac aat att ggc tcc cag tac ctg ctc aac tgg tgt gtg cag atc gca      384
```

-continued

```
Asp Asn Ile Gly Ser Gln Tyr Leu Leu Asn Trp Cys Val Gln Ile Ala
            115                 120                 125 aag ggc atg aac tac ttg gag gac cgt cgc ttg gtg cac cgc gac ctg     432
Lys Gly Met Asn Tyr Leu Glu Asp Arg Arg Leu Val His Arg Asp Leu
        130                 135                 140 gca gcc agg aac gta ctg gtg aaa aca ccg cag cat gtc aag atc aca     480
Ala Ala Arg Asn Val Leu Val Lys Thr Pro Gln His Val Lys Ile Thr
145                 150                 155                 160 gat ttt ggg ctg gcc aaa ctg ctg ggt gcg gaa gag aaa gaa tac cat     528
Asp Phe Gly Leu Ala Lys Leu Leu Gly Ala Glu Glu Lys Glu Tyr His
                165                 170                 175 gca gaa gga ggc aaa gtg cct atc aag tgg atg gca ttg gaa tca att     576
Ala Glu Gly Gly Lys Val Pro Ile Lys Trp Met Ala Leu Glu Ser Ile
            180                 185                 190 tta cac aga atc tat acc cac cag agt gat gtc tgg agc tac ggg gtg     624
Leu His Arg Ile Tyr Thr His Gln Ser Asp Val Trp Ser Tyr Gly Val
        195                 200                 205 acc gtt tgg gag ttg atg acc ttt gga tcc aag cca tat gac gga atc     672
Thr Val Trp Glu Leu Met Thr Phe Gly Ser Lys Pro Tyr Asp Gly Ile
    210                 215                 220 cct gcc agc gag atc tcc tcc atc ctg gag aaa gga gaa cgc ctc cct     720
Pro Ala Ser Glu Ile Ser Ser Ile Leu Glu Lys Gly Glu Arg Leu Pro
225                 230                 235                 240 cag cca ccc ata tgt acc atc gat gtc tac atg atc atg gtc aag tgc     768
Gln Pro Pro Ile Cys Thr Ile Asp Val Tyr Met Ile Met Val Lys Cys
                245                 250                 255 tgg atg ata gac gca gat agt cgc cca aag ttc cgt gag ttg atc atc     816
Trp Met Ile Asp Ala Asp Ser Arg Pro Lys Phe Arg Glu Leu Ile Ile
            260                 265                 270 gaa ttc tcc aaa atg gcc cga gac ccc cag cgc tac ctt gtc att cag     864
Glu Phe Ser Lys Met Ala Arg Asp Pro Gln Arg Tyr Leu Val Ile Gln
        275                 280                 285 ggg gat gaa aga atg cat ttg cca agt cct aca gac tcc aac ttc tac     912
Gly Asp Glu Arg Met His Leu Pro Ser Pro Thr Asp Ser Asn Phe Tyr
    290                 295                 300 cgt gcc ctg atg gat gaa gaa gac atg gac gac gtg gtg gat gcc gac     960
Arg Ala Leu Met Asp Glu Glu Asp Met Asp Asp Val Val Asp Ala Asp
305                 310                 315                 320 gag tac ctc atc cca cag cag ggc                                     984
Glu Tyr Leu Ile Pro Gln Gln Gly
                325

<210> SEQ ID NO 2
<211> LENGTH: 328
<212> TYPE: PRT
<213> ORGANISM: Homo sapiens

<400> SEQUENCE: 2

Ser Gly Glu Ala Pro Asn Gln Ala Leu Leu Arg Ile Leu Lys Glu Thr
1               5                   10                  15

Glu Phe Lys Lys Ile Lys Val Leu Gly Ser Gly Ala Phe Gly Thr Val
            20                  25                  30

Tyr Lys Gly Leu Trp Ile Pro Glu Gly Glu Lys Val Lys Ile Pro Val
        35                  40                  45

Ala Ile Lys Glu Leu Arg Glu Ala Thr Ser Pro Lys Ala Asn Lys Glu
    50                  55                  60

Ile Leu Asp Glu Ala Tyr Val Met Ala Ser Val Asp Asn Pro His Val
65                  70                  75                  80
```

```
Cys Arg Leu Leu Gly Ile Cys Leu Thr Ser Thr Val Gln Leu Ile Thr
            85              90                  95
Gln Leu Met Pro Phe Gly Cys Leu Leu Asp Tyr Val Arg Glu His Lys
            100             105                 110
Asp Asn Ile Gly Ser Gln Tyr Leu Leu Asn Trp Cys Val Gln Ile Ala
            115             120                 125
Lys Gly Met Asn Tyr Leu Glu Asp Arg Arg Leu Val His Arg Asp Leu
            130             135                 140
Ala Ala Arg Asn Val Leu Val Lys Thr Pro Gln His Val Lys Ile Thr
145                 150                 155                 160
Asp Phe Gly Leu Ala Lys Leu Leu Gly Ala Glu Glu Lys Glu Tyr His
                165             170                 175
Ala Glu Gly Gly Lys Val Pro Ile Lys Trp Met Ala Leu Glu Ser Ile
                180             185                 190
Leu His Arg Ile Tyr Thr His Gln Ser Asp Val Trp Ser Tyr Gly Val
            195             200                 205
Thr Val Trp Glu Leu Met Thr Phe Gly Ser Lys Pro Tyr Asp Gly Ile
        210             215                 220
Pro Ala Ser Glu Ile Ser Ser Ile Leu Glu Lys Gly Glu Arg Leu Pro
225                 230                 235                 240
Gln Pro Pro Ile Cys Thr Ile Asp Val Tyr Met Ile Met Val Lys Cys
                245             250                 255
Trp Met Ile Asp Ala Asp Ser Arg Pro Lys Phe Arg Glu Leu Ile Ile
                260             265                 270
Glu Phe Ser Lys Met Ala Arg Asp Pro Gln Arg Tyr Leu Val Ile Gln
            275             280                 285
Gly Asp Glu Arg Met His Leu Pro Ser Pro Thr Asp Ser Asn Phe Tyr
290                 295                 300
Arg Ala Leu Met Asp Glu Glu Asp Met Asp Asp Val Val Asp Ala Asp
305                 310                 315                 320
Glu Tyr Leu Ile Pro Gln Gln Gly
                325
```

METHODS AND USE OF BIFUNCTIONAL ENZYME-BUILDING CLAMP-SHAPED MOLECULES

CROSS-REFERENCE TO RELATED APPLICATIONS

This application is the National Stage of International Application No. PCT/US2012/029410, filed Mar. 16, 2012, which claims the benefit of U.S. Provisional Application No. 61/453,682, filed Mar. 17, 2011, and U.S. Provisional Application No. 61/486,453, filed May 16, 2011, the disclosures of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 14, 2012, is named UPN-5734.txt and is 8,152 bytes in size.

TECHNICAL FIELD

This invention is in the fields of cancer therapy. More particularly it concerns compounds which are useful agents for inhibiting cell proliferative disorders, especially those disorders characterized by over activity and/or inappropriate activity of a EGFR, including EGFR-related cancers, and methods for treating these disorders.

BACKGROUND

The epidermal growth factor receptor (EGFR) is the cell-surface receptor for members of the epidermal growth factor family (EGF-family) of extracellular protein ligands.

Abberrant EGFR activation, resulting in EGFR overexpression (known as upregulation) or overactivity is strongly implicated in a cancers, including lung cancer, anal cancers and glioblastoma multiforme, and is already the target of several anti-cancer therapeutics. Mutations, amplifications or misregulations of EGFR or family members are implicated in about 30% of all epithelial cancers.

The identification of EGFR as an oncogene has led to the development of anticancer therapeutics directed against EGFR. Two major strategies have been used for suppressing aberrant EGFR signalling: antibody targeting of the receptor ectodomain and small molecule inhibition of the tyrosine kinase domain. The antibody approach provides high target specificity, but has limitations and challenges in drug development because of the protein nature of the therapeutic agent, including cost and delivery. Cetuximab and panitumumab are examples of monoclonal antibody inhibitors. Other monoclonals in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method of inhibiting abberant EGFR signalling is to use small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors.

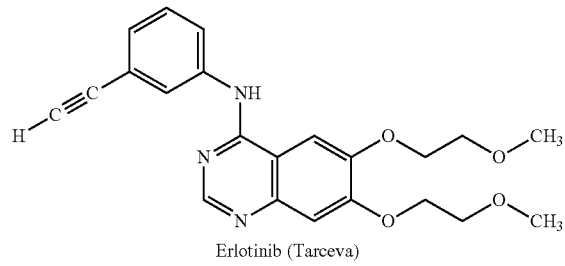
Erlotinib (Tarceva)

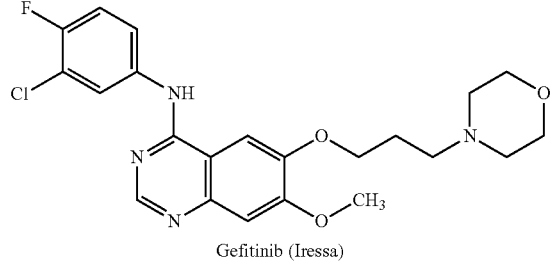
Gefitinib (Iressa)

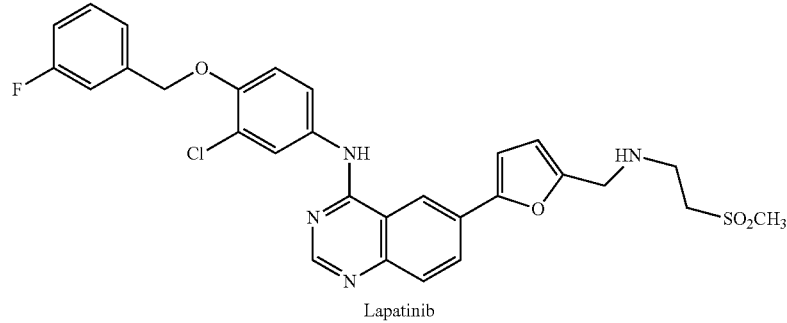
Lapatinib

The advantages of small-molecule drugs over therapeutic proteins include the ease of manufacturing and administration, the potential for oral dosing, low immunogenity and applicability to a wider range of disease targets, including those inside the cell. Indeed, small molecule inhibitors of the tyrosine kinase domain of EGFR (i.e., Iressa®, Tarceva®, and Tykerb®) have been successfully developed as drugs, which directly target the EGFR. But not all patients can benefit from such drugs. Patients can be been divided into EGFR positive and negative, based upon whether a tissue test shows a mutation. One of the most common mutations that sensitizes tumors to small molecule tyrosine kinase inhibitors is the so-called L858R mutation, wherein Leu-858 in the EGFR peptide sequence is replaced by an Arg-858 (so-called "L858R mutation"). EGFR positive patients have shown an impressive 60% response rate which exceeds the response rate for conventional chemotherapy. For example, see Jackman D M, et al., "Impact of epidermal growth factor receptor and KRAS mutations on clinical outcomes in previously untreated non-small cell lung cancer patients: results of an online tumor registry of clinical trials". *Clin. Cancer Res.* 15 (16): 5267-73 (August 2009). However, this mutation which allows for this success exists on only in a small sub-population (ca. 5%) of non-small cell lung cancer patients that harbor this particular mutation in the tyrosine kinase domain of EGFR.

There is a need for small molecule pharmaceuticals which regulate the overexpression of EGFR so as to inhibit cell proliferative disorders characterized by over-activity and/or inappropriate activity of EGFR in a wider population of patients suffering from such disorders, including EGFR-related cancers.

SUMMARY

The present disclosure provides multi-functional small molecule compounds wherein one functionality is capable of binding to the kinase domain of EGFR, so as to mimic the drug-sensitizing effect of the EGFR kinase domain mutations, and the other functionality is at the same time capable of binding to a proximate binding site so as to inhibit aberrant cell proliferation, differentiation, or survival. In certain embodiments of this invention, these compounds when contacted with EGFR and tested using tyrosine-specific antibody provides for enhanced constitutive phosphorylation of total EGFR as well as enhanced constitutive phosphorylation of Tyr 845 and/or Tyr 1068, but have no or little effect on constitutive phosphorylation of Tyr 992.

The invention provides for compound having a structure of Formula I:

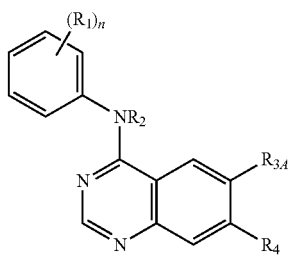

(I)

wherein
$R_1$ is independently H, optionally substituted amino, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted benzyloxy, cyano, halo, hydroxy, nitro, optionally substituted phenoxy, or mono-, di-, or trifluoromethyl;
n is 1, 2, or 3;
$R_2$ is independently H or $C_{1-3}$-alkyl;
$R_{3A}$ is —$OR_{5A}$, —$NR_2R_{5A}$, —$SR_{5A}$, —$C(O)R_{5A}$, —$C(O)OR_{5A}$, —$C(O)N(R_2)(R_{5A})$, —$OC(O)R_{5A}$, $OC(O)OR_{5A}$, —$OC(O)NR_2R_{5A}$, —$NR_2C(O)R_{5A}$, —$NR_2C(O)OR_{5A}$;
$R_4$ is H, —$N(R_2)_2$, optionally substituted $C_{1-3}$-alkyl, optionally substituted $C_{1-3}$-alkoxy, cyano, halo, hydroxy, nitro, or mono-, di-, or trifluoromethyl;
$R_{5A}$ is —$(C_{1-4}$-alkyl$)$-X—$R_6$—$R_7$;
X is independently O, S, or $N(R_2)$;
$R_6$ is a bond or $C_{5-6}$ aryl or heteroaryl having 5-6 ring members;
$R_7$ is either a $C_{1-4}$-alkyl substituted by at least one —OH or —$C(O)OR_2$ or —$C(O)N(R_2)_2$, or a heteroaryl having 5 ring members, containing 1-3 heteroatoms and substituted by $R_2$ and either a halo-substituted benzyloxy or —X—$R_8$; and
$R_8$ is $C_{1-3}$ alkyl substituted by at least one —OH, —COOH, —$C(O)O$—$C_{1-4}$ alkyl, $C(O)N(R_2)_2$, or $C_{1-5}$ cycloalkyl;
or a pharmaceutically acceptable salt form thereof.

Additional embodiments provide that these compounds are also a product of the reaction between a compound of Formula III and a compound of Formula IV:

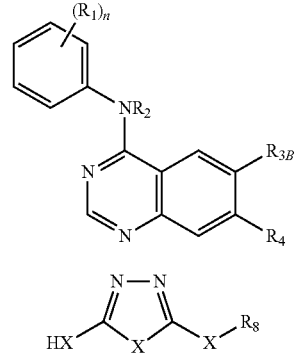

wherein
$R_1$ is independently H, optionally substituted amino, optionally substituted $C_{1-6}$ alkyl, optionally substituted $C_{1-6}$ alkoxy, optionally substituted $C_{1-6}$ alkenyl, optionally substituted $C_{1-6}$ alkynyl, optionally substituted benzyloxy, cyano, halo, hydroxy, nitro, optionally substituted phenoxy, or mono-, di-, or trifluoromethyl;
n is 1, 2, or 3;
$R_2$ is independently H or $C_{1-3}$-alkyl;
$R_{3B}$ is —$OR_{5B}$, —$NR_2R_{5B}$, —$SR_{5B}$, —$C(O)R_{5B}$, —$C(O)OR_{5B}$, —$C(O)N(R_2)(R_{5B})$, —$OC(O)R_{5B}$, —$OC(O)OR_{5B}$, —$OC(O)NR_2R_{5B}$, —$NR_2C(O)R_{5B}$, or —$NR_2C(O)OR_{5B}$;
$R_4$ is H, —$N(R_2)_2$, optionally substituted $C_{1-3}$-alkyl, optionally substituted $C_{1-3}$-alkoxy, cyano, halo, hydroxy, nitro, or mono-, di-, or trifluoromethyl;
$R_{5B}$ is —$(C_{0-4}$-alkyl$)$-L, wherein L is a leaving group;
X is independently O, S, or $N(R_2)$; and
$R_8$ is $C_{1-3}$ alkyl substituted by at least one —OH, —COOH, —$C(O)O$—$C_{1-4}$ alkyl, $C(O)N(R_2)_2$, or $C_{3-5}$ cycloalkyl;
or a pharmaceutically acceptable salt form thereof.

Other embodiments provide for pharmaceutical compositions comprising a multi-functional small molecule compound, as described above, in an amount effective to inhibit a cell proliferative disorder characterized by over-activity and/or inappropriate activity of a EGF receptor. In other embodiments, pharmaceutical compositions comprise at least one compound having a structure of Formula (I), or a product of the reaction between a compound of Formula III and a compound of Formula IV, as described above.

In still other embodiments, these compounds are used for the preparation of medicaments for the inhibition of a cell proliferative disorder characterized by over-activity and/or inappropriate activity of an epidermal growth factor receptor (EGFR).

Other embodiments provide methods of inhibiting a cell proliferative disorder characterized by over-activity and/or inappropriate activity of a receptor comprising administering to a patient in need of such treatment a pharmaceutically effective amount of at least one of these compounds. Additionally, the invention provides methods of treating a patient having a disease characterized by over-activity and/or inappropriate activity of an epidermal growth factor receptor (EGFR), comprising the step of administering to said patient a pharmaceutically effective amount of at least one of these compounds.

BRIEF DESCRIPTION OF THE DRAWINGS

The figures provided herein are intended to be illustrative and not limiting.

FIG. 1 illustrates the binding site and possible orientation of C318 in complex with EGFR kinase. (A) shows a theoretical electron density map of the complex. (B) illustrates a possible clamp-shaped orientation of C318 bound to EGFR kinase.

FIG. 4 shows cell cultures comparing the effects of C318 and Tarceva® at 0.1 µM concentrations on anchorage independent growth of NE91 cells. The cultures show soft agar colony formations after three weeks with no treatment (A), with Tarceva® (B) and with C318 (C). (D) shows quanitative counts for each of these cultures.

FIG. 5 identifies wild-type amino acid (SEQ ID NO: 2) and corresponding nucleic acid sequences (SEQ ID NO: 1) for the human EGFR kinase domain. Residue number 1 of SEQ ID NOS: 1 and 2 corresponds to residue 695 of FIG. 5, and the remaining residues are numbered consecutively in a corresponding manner (for example, the 858 position in FIG. 5, corresponds to the 164 position of SEQ ID NOS: 1 and 3). Further, SEQ ID NO: 3 provides an amino acid sequence of human EGFR wherein the leucine residue at position 164 is substituted with arginine (L858R mutation).

DETAILED DESCRIPTION OF ILLUSTRATIVE EMBODIMENTS

Figure 2:
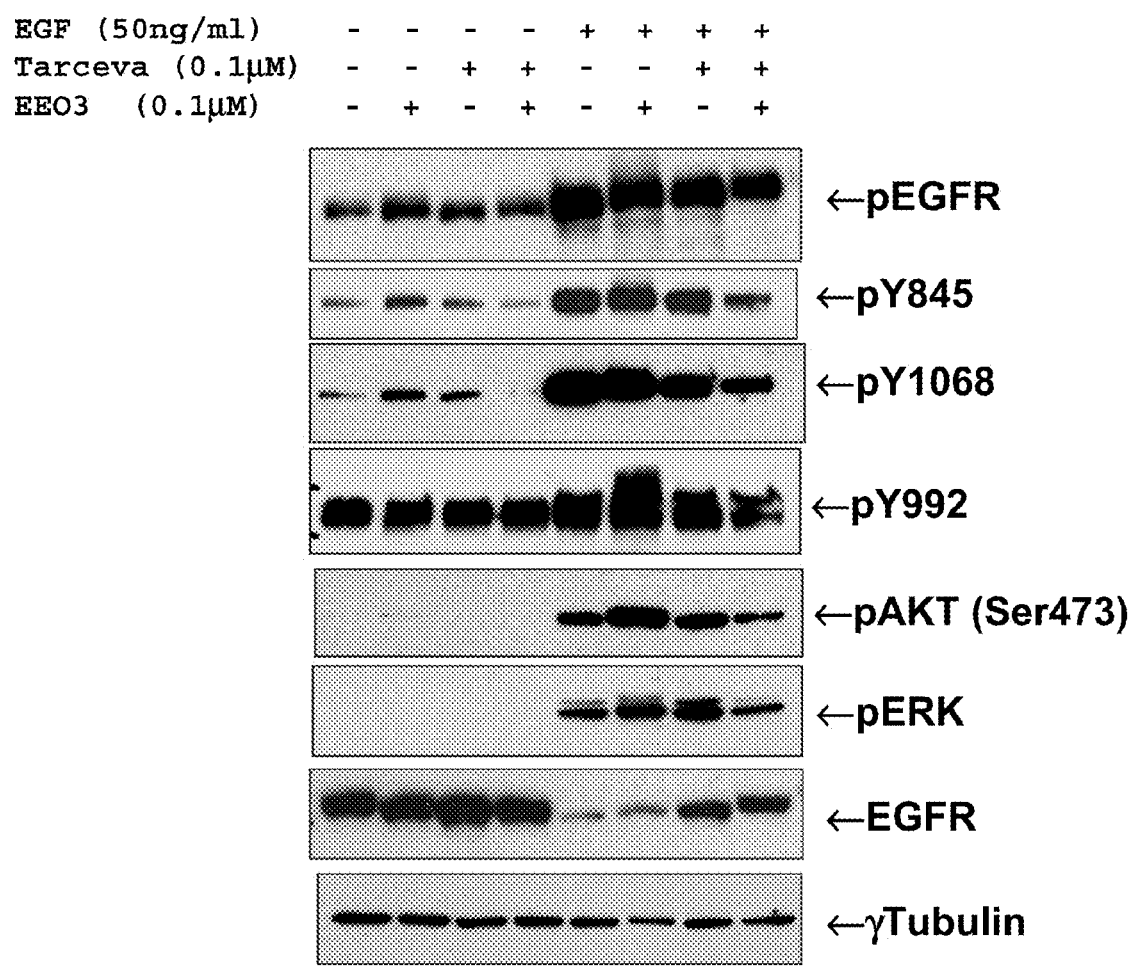
FIG. 2 illustrates the effect of an exemplary mutation mimicking compound (EEO3) and Tarceva® on EGFR phosphorylation and downstream signaling (Example 3).

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and to the resulting pharmaceutical compositions and methods of manufacture and use.

The present invention relates to use of small molecule compounds to modulate or inhibit the activity of a receptor tyrosine kinase.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges include each and every value within that range.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Finally, while an embodiment may be described as part of a series of steps or part of a more general composition or structure, each said step may also be considered an independent embodiment in itself.

Overview

The present invention describes multi-functional small molecule, low molecular weight compounds wherein one functionality is capable of binding to the kinase domain of EGFR, so as to mimic the drug-sensitizing effect of the EGFR kinase domain mutations, this binding site is defined by the cavity between the residues G719-F723, V726, K745, L747, A755, E758, I759, D761, E762, C797, L799, D800, D837, R841, N842, D855, G857, L858, K875, P877 of the amino acid sequence of human EGFR shown in FIG. 5 (Note that the corresponding residues in SEQ. ID NOS.: 1-2 are G25-F29, V32, K51, L53, A61, E64, I65, D67, E68, C103, L105, D106, D143, R841, N148, D161, G163, L164, K181, P183), and the other functionality is at the same time capable of binding to a proximate binding site (the ATP binding site) so as to inhibit aberrant cell proliferation, differentiation, or survival.

The former functionality (i.e., the ability to mimic the drug-sensitizing effect of the EGFR kinase domain mutations is the subject of U.S. Patent Application Ser. Nos. 61/453,626 and 61/454,083, filed Mar. 17, 2011 and Mar. 18, 2011, respectively and each of which is incorporated by reference herein in its entirety for all purposes.

The compounds of the present invention can be identified by their binding affinity to the target cavity and their overall pharmacological activity. At a first level, this can be accomplished through use of commercial software packages which are capable of identifying low-energy binding modes of small molecules, or ligand, within the identified target cavity. One non-limiting example of such software is the widely distributed DOCK software, version 4.0, Ewing, et al., "DOCK 4.0: search strategies for automated molecular docking of flexible molecule databases," J. Comput. Aided Mol. Des., 15: 411-428 (2001), which is incorporated by reference herein in its entirety. The DOCK software is but one commercial software packages used for this purpose, and it is expected that other such software packages may be useful for this purpose.

The DOCK screening software, and other similar programs, generally do not provide absolute estimates of binding affinities, rather providing relative rankings. Embodiments of the present invention, then, include those compounds characterized by having relative binding affinities, as estimated by the DOCK software, version 4.0, of at least as high as those exhibited by any of the specific compounds described herein.

The latter functionality—i.e., the ability to inhibit such aberrant cell proliferation, differentiation, or survival—has been previously studied by others. In the present case, it is expected that any structure known independently to exhibit this type of activity can be used for this purpose. Consistent with this behavior, various embodiments of the present invention include those compounds which act on EGFR to replicate the appearance of the L858R mutation; i.e., compounds whose reaction with EGFR result in enhanced constitutive phosphorylation of total EGFR as well as enhanced constitutive phosphorylation of Tyr 845 and/or Tyr 1068, but have no or little effect on constitutive phosphorylation of Tyr 992, when tested as described below.

As experiments described in U.S. Patent Application Ser. No. 61/453,626, filed Mar. 17, 2011, which is incorporated by reference herein for all purposes, including the compounds and characterizations of same described therein, have shown that small molecules targeted to the cavity adjacent to the binding site (the ATP binding site) can be used effectively to restrain the EGFR kinase in the active conformation resulting in the enhanced inhibition of EGFR by traditional tyrosine kinase inhibitors. Linking these compounds with traditional inhibitors targeted to the ATP-binding site (e.g., Erlotinib, Gefitinib, and Lapatinib) can produce bifunctional enzyme-binding clamp-shaped molecules (EBCMs) with a dual mechanism of action. The mutation-mimicking part (MMP) of the EBCM restrains the enzyme in an active-like conformation resulting in alterations of the enzyme signaling properties. In the case of EGFR kinase, introduction of the MMP in EGFR-expressing tumor cells can activate the enzyme and at the same time result in higher dependence of tumor cell survivor on the EGFR signaling pathway. These effects are similar to those produced by drug-sensitizing mutations. The tyrosine kinase inhibitor part of the EBCM inhibits the enzyme by occupying the ATP-binding site resulting in effective suppression of tumor growth. Since enzyme-activating mutations have been described for numerous enzymes, combining mutation mimicking compounds with traditional enzyme inhibitors into single EBCM molecules may represent a general two-step approach to inhibit enzymes while simultaneously changing their signaling properties and increasing the importance of the enzymes for cell survival.

Even though the molecules described herein were designed to operate by this mode of interaction with EGFR, the invention is not limited to this mode of interaction. The molecules may additionally or alternatively operate by other modes to inhibit the over-activity and/or inappropriate activity of an epidermal growth factor receptor (EGFR).

Compounds

With this in mind, various embodiments of this invention provides compounds having a structure of Formula I:

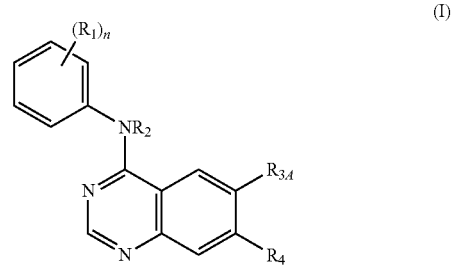

wherein
the substitution patterns of the anilinoquinazoline moiety, including $(R_1)_n$, $R_2$, and $R_4$, are the same as the substituents and spatial arrangement thereof as in Erlotinib, Gegitinib, or Lapatinib, or are consistent with, or as provided by, the structures and substitutions described in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib), each of which is incorporated by reference herein;

$R_{3A}$ is —$OR_{5A}$, —$NR_2R_{5A}$, —$SR_{5A}$, —$C(O)R_{5A}$, —$C(O)OR_{5A}$, —$C(O)N(R_2)(R_{5A})$, —$OC(O)R_{5A}$, —$OC(O)OR_{5A}$, —$OC(O)NR_2R_{5A}$, —$NR_2C(O)R_{5A}$, —$NR_2C(O)OR_{5A}$;

$R_{5A}$ is —$(C_{1-4}$-alkyl)-X—$R_6$—$R_7$;

X is independently O, S, or $N(R_2)$;

$R_6$ is a bond or $C_{5-6}$ aryl or heteroaryl having 5-6 ring members;

$R_7$ is either a $C_{1-4}$-alkyl substituted by at least one —OH or —$C(O)OR_2$ or —$C(O)N(R_2)_2$, or a heteroaryl having 5-6 ring members, containing 1-3 heteroatoms and substituted by $R_2$ and either a halo-substituted benzyloxy or —X—$R_8$; and $R_8$ is $C_{1-3}$ alkyl substituted by at least one —OH, —COOH, —$C(O)O$—$C_{1-4}$ alkyl, —$N(R_2)_2$, —$C(O)N(R_2)_2$, or $C_{1-5}$ cycloalkyl;

or a pharmaceutically acceptable salt form thereof.

Other embodiments of this invention provide a product of the reaction between a compound of Formula (III) and a compound of Formula (IV):

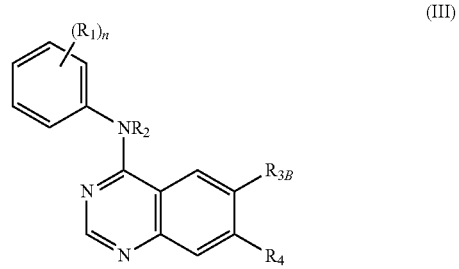

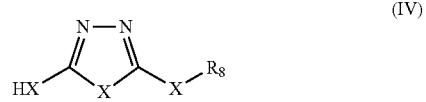

wherein
the substitution patterns of the anilinoquinazoline moiety, including $(R_1)_n$, $R_2$, and $R_4$ are the same as the substituents and spatial arrangement thereof as in Erlotinib, Gegitinib, or Lapatinib, or are consistent with, or as provided by, the structures and substitutions described in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib), each of which is incorporated by reference herein;
$R_{3B}$ is —$OR_{5B}$, —$NR_2R_{5B}$, —$SR_{5B}$, —$C(O)R_{5B}$, —$C(O)OR_{5B}$, —$C(O)N(R_2)(R_{5B})$, —$OC(O)R_{5B}$, —$OC(O)OR_{5B}$, —$OC(O)NR_2R_{5B}$, —$NR_2C(O)R_{5B}$, —$NR_2C(O)OR_{5B}$;
$R_{5B}$ is —$(C_{0-4}$-alkyl)-L, wherein L is a leaving group, susceptible to nucleophilic displacement;
X is independently at each occurrence O, S, or $N(R_2)$; and
$R_8$ is $C_{1-3}$ alkyl substituted by at least one —OH, —COOH, —C(O)O—$C_{1-4}$ alkyl, —$C(O)N(R_2)_2$, —$N(R_2)_2$, or $C_{3-5}$ cycloalkyl;
or a pharmaceutically acceptable salt form thereof.

Additional embodiments within these frameworks include those compounds wherein $R_1$ is independently H, optionally substituted amino, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted benzyloxy, cyano, halo, hydroxy, nitro, optionally substituted phenoxy, or mono-, di-, or trifluoromethyl;
n is 1, 2, or 3;
$R_2$ is independently H or $C_{1-3}$-alkyl; and $R_4$ is H, —$N(R_2)_2$, optionally substituted $C_{1-3}$-alkyl, optionally substituted $C_{1-3}$-alkoxy, cyano, halo, hydroxy, nitro, or mono-, di-, or trifluoromethyl.

In various embodiments, the compounds of Formula (I) or the compounds resulting from the reaction of compounds of Formula (III) and Formula (IV) include those wherein each $R_1$ is independently H, optionally substituted $C_{2-6}$ alkynyl, optionally substituted benzyloxy, or halo. Other embodiments include those wherein each $R_1$ is independently Cl or F. Still other embodiments include those wherein $R_2$ is H. Independent embodiments provide compounds of Formula (I) or the compounds resulting from the reaction of compounds of Formula (III) and Formula (IV) wherein $R_1$ is ethynyl, n is 1, and $R_2$ is H, wherein n is 2, each $R_1$ is independently Cl or F, and $R_2$ is H, and wherein one $R_1$ is halo substituted benzyloxy, one $R_1$ is halo, and $R_2$ is H.

Other embodiments provide that $R_4$ is H, —$N(R_2)_2$, optionally substituted $C_{1-3}$-alkyl, optionally substituted $C_{1-3}$-alkoxy, cyano, halo, hydroxy, nitro, or mono-, di-, or trifluoromethyl. Compounds wherein $R_4$ is H are preferred.

In certain embodiments, the compounds having the general structures of Formula (I) include those wherein $R_{3A}$ is —$OR_{5A}$, —$NR_2R_{5A}$, —$SR_{5A}$, —$C(O)R_{5A}$, —$C(O)OR_{5A}$, —$C(O)N(R_2)(R_{5A})$, —$OC(O)R_{5A}$, —$OC(O)OR_{5A}$, —$OC(O)NR_2R_{5A}$, —$NR_2C(O)R_{5A}$, or —$NR_2C(O)OR_{5A}$. Preferred embodiments include those wherein $R_{3A}$ is —$NR_2C(O)R_{5A}$. In these cases, $R_{5A}$ is —$(C_{1-4}$-alkyl)-X—$R_6$—$R_7$, where $R_6$ is a bond or $C_{5-6}$ aryl or $C_{5-6}$ heteroaryl and X is independently O, S, or $N(R_2)$. In certain embodiments, $R_6$ is a $C_6$ heteroaryl and $R_7$ is a $C_5$ heteroaryl containing 1-3 heteroatoms and substituted by $R_2$ and a halo-substituted benzyloxy.

Additional independent embodiments also include those compounds having the general structures of Formula (I) wherein $R_{5A}$ is —$CH_2$—S—$R_6$—$R_7$. More specific independent embodiments include those compounds having structures of Formula (I) wherein $R_2$ is H, $R_{3A}$ is —$NR_2C(O)R_{5A}$, $R_4$ is H, and $R_{5A}$ is —$CH_2$—S—$R_6$—$R_7$, and additionally (a) $R_1$ ethynyl, n is 1, (b) n is 2, each $R_1$ is independently Cl or F, and (c) n is 2, one $R_1$ is halo substituted benzyloxy, one $R_1$ is halo, and $R_2$ is H.

In certain embodiments, the compounds resulting from the reaction between compounds of Formula (III) and compounds of Formula (IV) include those wherein $R_{3B}$ is —$OR_{5B}$, —$NR_2R_{5B}$, —$SR_{5B}$, —$C(O)R_{5B}$, —$C(O)OR_{5B}$, —$C(O)N(R_2)(R_{5B})$, —$OC(O)R_{5B}$, —$OC(O)OR_{5B}$, —$OC(O)NR_2R_{5B}$, —$NR_2C(O)R_{5B}$, or —$NR_2C(O)OR_{5B}$. Preferred embodiments include those wherein $R_{3B}$ is —$NR_2C(O)R_{5B}$.

Additional independent embodiments also include those compounds resulting from the reaction between compounds of Formula (III) and compounds of Formula (IV) wherein $R_{5B}$ is —$CH_2$-L, where L is preferably a halide, or Cl. More specific independent embodiments include those compounds resulting from the reaction between compounds of Formula (III) and compounds of Formula (IV) wherein $R_2$ is H, $R_{3B}$ is —$NR_2C(O)R_{5B}$, $R_4$ is H, and $R_{5B}$ is —$CH_2$—Cl, and additionally (a) $R_1$ is ethynyl, n is 1, (b) n is 2, each $R_1$ is independently Cl or F, and (c) n is 2, one $R_1$ is halo substituted benzyloxy, one $R_1$ is halo, and $R_2$ is H.

Specific embodiments of the present invention containing the preceding substructures also provide that $R_7$ is either a $C_{1-4}$-alkyl substituted by at least one —OH or —$C(O)OR_2$ or —$C(O)N(R_2)_2$, or a $C_5$ heteroaryl containing 1-3 heteroatoms and substituted by $R_2$ and either a halo-substituted benzyloxy or —X—$R_8$. In all cases wherein a substitution pattern provides for a plurality of hydroxyl, carboxy, or amide group groups, separate embodiments provide that these groups may exist in their cyclic dehydrated forms—e.g., as cyclic anhydrides, lactones, or lactams. For example:

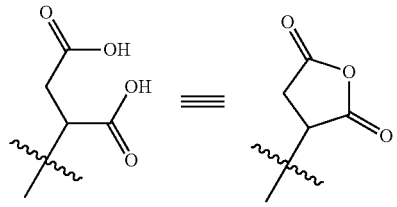

More specific embodiments provide that $R_6$ is a bond and $R_7$ is a $C_{1-4}$-alkyl substituted by at least one hydroxyl or carboxy, more specifically wherein $R_6$ is a bond and $R_7$ is a $CH_2CH_2OH$ or $CH_2CH_2COOH$.

Other embodiments of the present invention containing any of the preceding substructures provide that $R_6$ is a bond and $R_7$ is a $C_5$ heteroaryl containing 1-3 heteroatoms and substituted by $R_2$ and —X—$R_8$, where X is O, S, or $N(R_2)$, an especially wherein X is S.

The invention provides that $R_8$ may be $C_{1-3}$ alkyl substituted by at least one —OH, —COOH, —C(O)O—$C_{1-4}$ alkyl, —$C(O)N(R_2)_2$, or $C_{1-5}$ cycloalkyl. Those embodiments wherein $R_8$ is —$CH_2COOR_2$, —$CH(CH_3)COOR_2$, or —$CH_2$-$cC_3H_7$ are preferred.

Other embodiments provide for compounds and formulations comprising compounds having a structure Formula (IA):

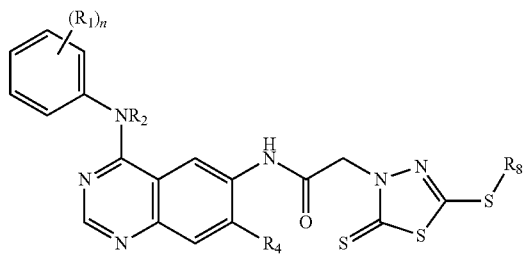

(IA)

where the $(R_1)_n$, $R_2$, $R_4$, and $R_8$, and the various embodiments involving their permutations, are as provided above.

Still other embodiments provide for compounds and formulations comprising compounds having a structure Formula (IB):

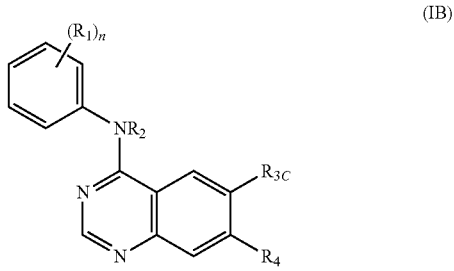

(IB)

wherein
the substitution patterns of the anilinoquinazoline moiety, including $(R_1)_n$, $R_2$, and $R_4$ are the same as the substituents and spatial arrangement thereof as in Erlotinib, Gegitinib, or Lapatinib, or are consistent with, or as provided by, the structures and substitutions described in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib), each of which is incorporated by reference herein; and $R_{3C}$ is a structure substantially as described in U.S. Patent Application Ser. Nos. 61/453,626 and 61/454,083, tethered to the anilinoquinazoline moiety by a 0-6 chain atom linkage.

Generally terms are to be given their plain and ordinary meaning such as understood by those skilled in the art, in the context in which they arise. To avoid any ambiguity, however, several terms are described herein.

Whenever a group of this invention is described as being "optionally substituted" that group may be unsubstituted or substituted with one or more of the substituents described for that group. Likewise, when a group is described as being "unsubstituted or substituted," if substituted, the substituent may be selected from the same group of substituents. Unless otherwise indicated, when a substituent is deemed to be "optionally substituted," or "substituted" it is meant that the substituent is a group that may be substituted with one or more group(s) individually and independently selected.

Each of the following terms (e.g., "alkyl," "heteroalkyl," "acyl," "alkoxy," "aryl," and "heteroaryl") include both substituted and unsubstituted forms of the indicated group, unless indicated otherwise.

The term "alkyl," by itself or as part of another substituent, means, unless otherwise stated, a straight or branched chain, or cyclic hydrocarbon group (cycloalkyl), or combination thereof, which may be fully saturated, mono- or polyunsaturated and can include di- and multivalent radicals, and can have a number of carbon atoms optionally designated (e.g., $C_{1-3}$ means one to three carbons). Examples of saturated hydrocarbon groups include, but are not limited to, groups such as methyl, ethyl, n-propyl, isopropyl.

As used herein, "alkenyl" refers to an alkyl group that contains in the straight or branched hydrocarbon chain one or more double bonds. Examples of alkenyl groups include, without limitation, vinyl ($CH_2$=CH—), allyl ($CH_3CH$=$CH_2$—), 1-propenyl, 2-propenyl, 1-butenyl, 2-butenyl; 1-pentenyl, 2-pentenyl, 3-pentenyl, 4-pentenyl, 3-methyl-1-butenyl, and the various isomers of hexenyl, heptenyl, octenyl, nonenyl, decenyl, undecenyl and dodecenyl.

As used herein, "alkynyl" refers to an alkyl group that contains in the straight or branched hydrocarbon chain one or more triple bonds. In the context of the present invention, substituted ethynyl groups are preferred.

Cycloalkyl groups of this invention may range from $C_3$ to $C_8$. A cycloalkyl group may be unsubstituted or substituted. If substituted, the substituent(s) may be selected from those indicated above with regard to substitution of an alkyl group.

An alkyl, alkenyl, or alkynyl group of this invention may be substituted or unsubstituted. When substituted, the substituent group(s) may be one or more group(s) independently selected from cycloalkyl, aryl, heteroaryl, heteroalicyclyl, hydroxy, alkoxy, aryloxy, mercapto, alkylthio, arylthio, cyano, halo, oxo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, amino or substituted amino, protected hydroxyl, protected amino, protected carboxy and protected amido groups.

As used herein, "acyl" refers to an "RC(=O)—." An acyl group may contain an alkyl or aryl moiety, in which case it may be referred to as a carboxyalkyl or carboxyaryl group, respectively. Examples of acyl groups include, without limitation, formyl, acetyl, propionyl, butyryl, pentanoyl, pivaloyl, hexanoyl, heptanoyl, octanoyl, nonanoyl, decanoyl, undecanoyl, dodecanoyl and benzoyl. Presently preferred acyl groups are acetyl and benzoyl.

An acyl group of this invention may be unsubstituted or substituted. When substituted, the substituent(s) may be selected from the same groups disclosed above with regard to alkyl group substitution.

The term "alkoxy" is used in its conventional sense, and refers to those alkyl groups attached to the remainder of the molecule via an oxygen atom. Alkoxy groups include, but are not limited to methoxy, ethoxy, propoxy, trifluoromethoxy and difluoromethoxy.

An "amide" is a chemical moiety with formula —(R)$_n$—C(O)NHR' or —(R)$_n$—NHC(O)R', where n is the number of alkylene carbons from 0-1, R and R' are independently selected from the group consisting of alkyl, cycloalkyl, aryl, heteroaryl (bonded through a ring carbon) and heteroalicyclic (bonded through a ring carbon). An amide may be an amino acid or a peptide molecule attached to a molecule of the present invention, thereby forming a prodrug.

Any amine, hydroxy, or carboxyl side chain on the compounds of the present invention can be esterified or amidified. Where embodiments describe such side chains, still further embodiments include those wherein these side chains are replaced by ester or amide analogs. The procedures and specific groups to be used to achieve this end is known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein in its entirety.

The term "0-6 chain atom linkage" refers to a linear arrangement of 0 to 6 C, N, O, or S atoms, connecting a structure substantially as described in U.S. Patent Application Ser. Nos. 61/453,626 and 61/454,083 and the anilinoquinazoline moiety of Formula (IA), where $(R_1)_n$, $R_2$, and $R_4$ are the same as the substituents and spatial arrangement thereof as in Erlotinib, Gegitinib, or Lapatinib, or are consistent with, or as provided by, the structures and substitutions described in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib). Such a linkage may include, without limitations, an alkyl, alkenyl, alkynyl, amine, amide, ester, ether, thio, thioether, or thioester moiety. A linear arrangement of atoms considered only those atoms aligned in the chain, so that, for example, an ester moiety, —C(O)—O—, contains two atoms in the chain, the carbonyl oxygen being not considered "in the linear arrangement of the chain" for atom count purposes. The term "structure substantially as described in U.S. Patent Application Ser. Nos. 61/453,626 and 61/454,083" refers to a moiety containing any one of the ring structure arrays described in either of these references, for example:

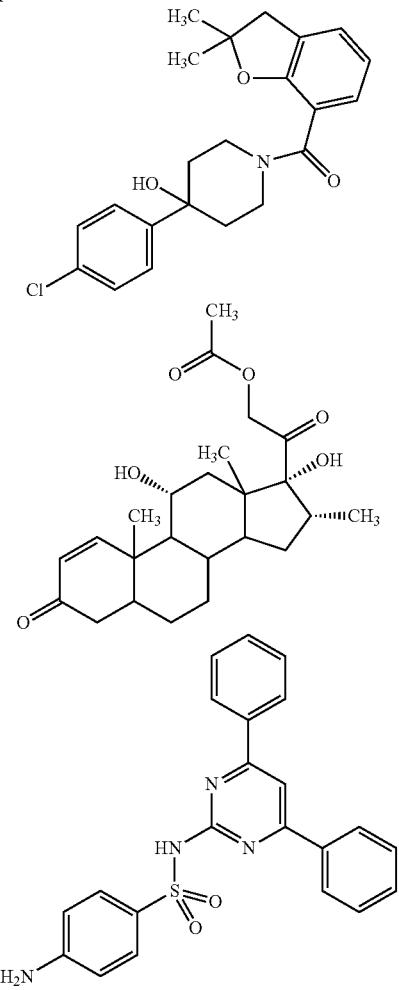

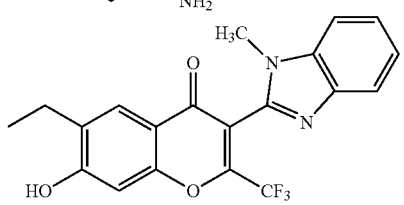

allowing for the connection to the 0-6 chain atom linkage by way of one of the functional groups of these compounds (e.g., halide coupling or attachment via amine nitrogen or alcohol, or ester oxygen).

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

As used herein, an "ether" refers to an "—C—O—C—" group wherein either or both carbons may independently be part of an alkyl, alkenyl, alkynyl, aryl, heteroaryl or heteroalicyclyl group. A "halogenated ether" refers to an ether in which the groups to either side of the oxygen are both alkyl substituted with halogen.

The terms "halo" or "halogen," by themselves or as part of another substituent, mean, unless otherwise stated, a fluorine, chlorine, bromine, or iodine atom. Preferred halogens are chloro and fluoro.

The term "heteroalkyl," by itself or in combination with another term, means, unless otherwise stated, a stable straight or branched chain, or cyclic hydrocarbon group, or combinations thereof, consisting of a number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

As used herein, "heteroaryl" refers to a ring that contains one or more heteroatoms selected from the group consisting of nitrogen, oxygen and sulfur in the ring and that has a fully delocalized pi-electron system. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

As used herein, the term "leaving group" refers to any moiety susceptible to nucleophilic substitution, especially $S_N2$ type nucleophilic substitution. Exemplary leaving groups include halides (Cl, Br, I, preferably Cl), tosylates, brosylates, nosylates, mesylates, and triflates. For example, see J. March, Advanced Organic Chemistry, $2^{nd}$ Ed., Chapter 10, 1977, which is incorporated by reference herein for this purpose The compounds of the present invention may also contain unnatural proportions of atomic isotopes at one or more of the atoms that constitute such compounds. For example, the compounds may be radio-labeled with radioactive isotopes, such as for example tritium ($^3H$), iodine-125 ($^{125}I$), carbon-11 ($^{11}C$), carbon-14 ($^{14}C$), nitrogen-13 ($^{13}N$), sulfur-35 ($^{35}S$), iodine-131 ($^{131}I$), or fluorine-18 ($^{18}F$). When indicated as such, radio-labeled molecules contain isotopes enriched above their natural abundances. Such radioisotopes can be prepared either by synthetic means using commercially available precursors and reactants generally recognized as providing by substitution the particular element of interest (e.g., halide substitution using radioactive halides) or by cyclotron irradiation of the pre-formed molecules. All isotopic variations of the compounds of the present invention, whether radioactive or not, are intended to be encompassed within the scope of the present invention.

As used herein, "phenyl" refers to a 6-member aryl group. The term "benzyloxy" refers to a 6-member aryl group attached to the main structure by a methylene group. A phenyl or benzyloxy group may be unsubstituted or substituted. When substituted the substituent(s) is/are one or more, preferably one or two, group(s) independently selected from the group consisting of halogen, hydroxy, protected hydroxy, cyano, nitro, alkyl, alkoxy, acyl, acyloxy, carboxy, protected carboxy, carboxymethyl, protected carboxymethyl, hydroxymethyl, protected hydroxymethyl, or amino or substituted amino.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

Synthetic Schemes

Unless defined otherwise, all technical and scientific terms used herein generally have the same meaning as commonly understood by one of ordinary skill in the art to which this invention belongs. Generally, the nomenclature used herein and the laboratory procedures in organic chemistry and nucleic acid chemistry and hybridization described below are those well-known and commonly employed in the art. The techniques and procedures are generally performed according to conventional methods in the art and various general references that are provided throughout this document. The nomenclature used herein and the laboratory procedures in analytical chemistry, and organic synthetic chemistry described below are those well-known and commonly employed in the art. Standard techniques, or modifications thereof, are used for chemical syntheses and chemical analyses.

In general, the chemistry of the anilinoquinazoline substructure is well developed. For those portion of the molecules which can be analogized to the substructures and substitutions of compounds described in U.S. Pat. Nos. 5,747, 498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713, 485; 6,727,256; 6,828,320; and 7,157,466 (corresponding to Lapatinib), each of which is incorporated by reference herein, these references provide sufficient teachings to enable the ordinary skilled artisan to make at least these portions of the molecules.

Additional methods are known to functionalize the fused phenyl ring of the quinazoline ring at the 6-position (i.e., the point of attachment of $R_{3B}$) with nitrogen, oxygen, or sulfur moieties in the requisite position, to which the types of functional groups described above for $R_{3B}$ may be attached (e.g., $-OR_{5B}$, $-NR_2R_{5B}$, $-SR_{5B}$, $-C(O)R_{5B}$, $-C(O)OR_{5B}$, $-C(O)N(R_2)(R_{5B})$, $-OC(O)R_{5B}$, $-OC(O)OR_{5B}$, $-OC(O)NR_2R_{5B}$, $-NR_2C(O)R_{5B}$, $-NR_2C(O)OR_{5B}$).

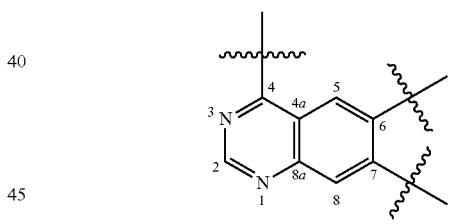

By contrast, the $R_{3A}$ pendant moieties are not known, at least in the context of the present invention. In this case, one exemplary scheme for construction of the certain embodiments of the present invention was accomplished using $S_N2$-type chemistry using commercially available nucleophilic thiol and model anilinoquinazoline precursors (details provided below in Example section):

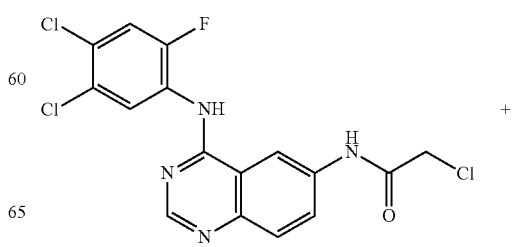

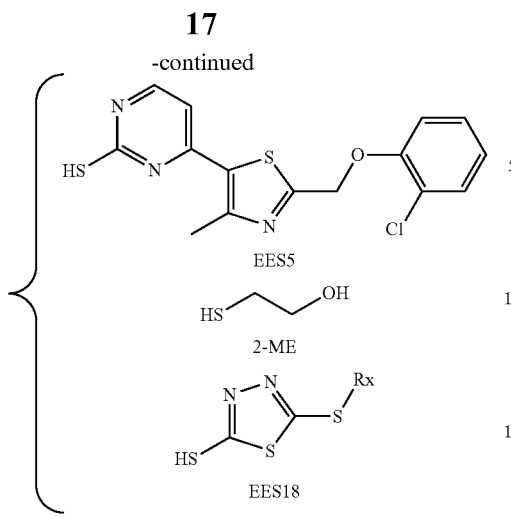

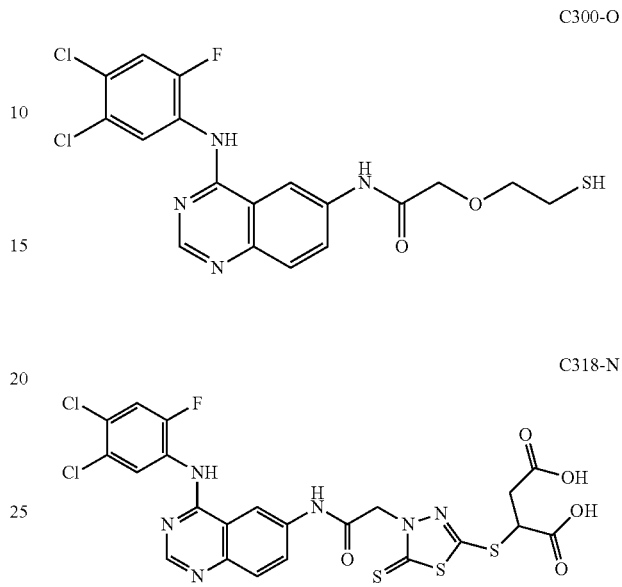

The reaction products of the synthetic scheme presented may also contain the following structural isomers of these products:

It should be appreciated that this approach (S$_N$2-type chemistry) may be generally applicable to prepare the compounds of Formula (I).

This synthetic method was used to prepare the corresponding compounds, each of which is a specific embodiment of the present invention:

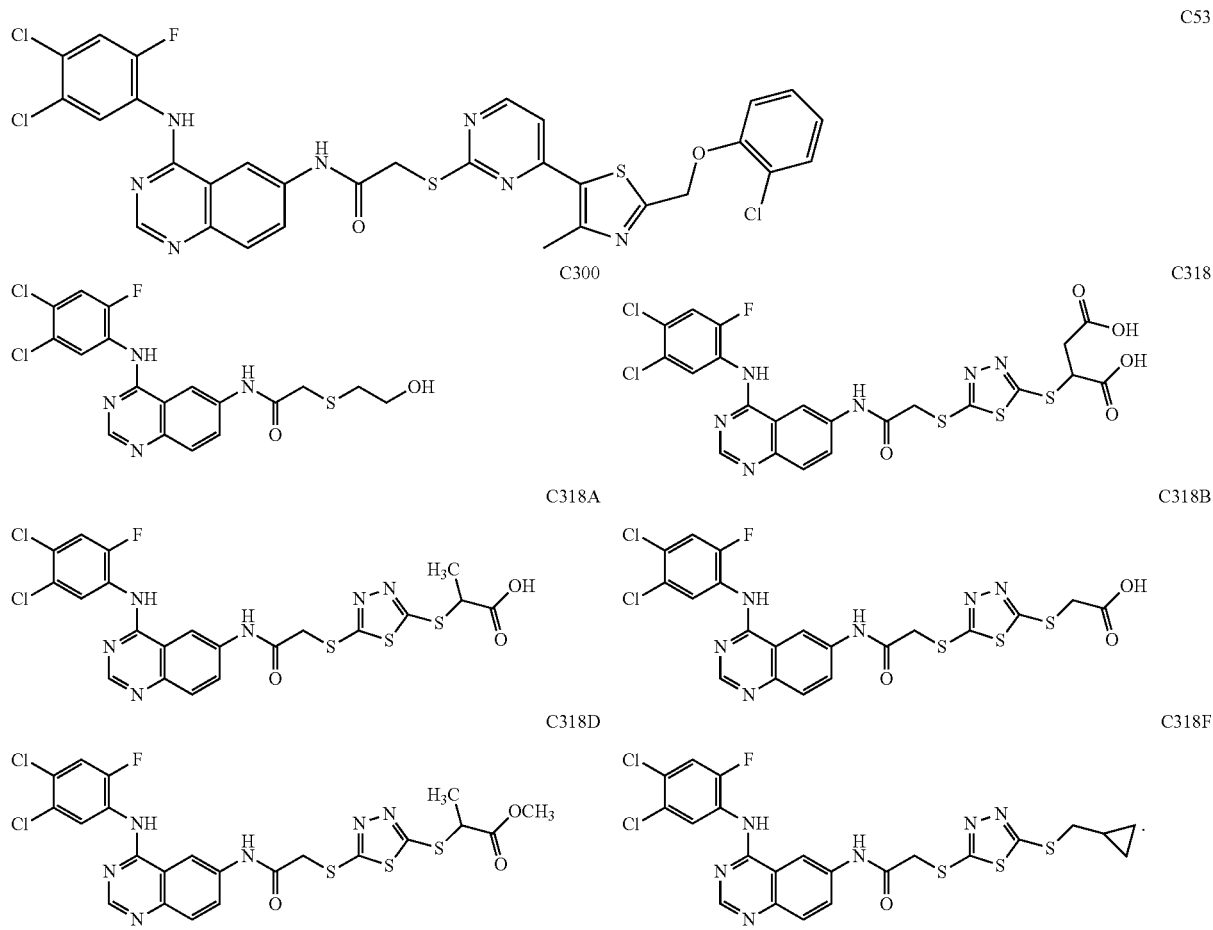

-continued

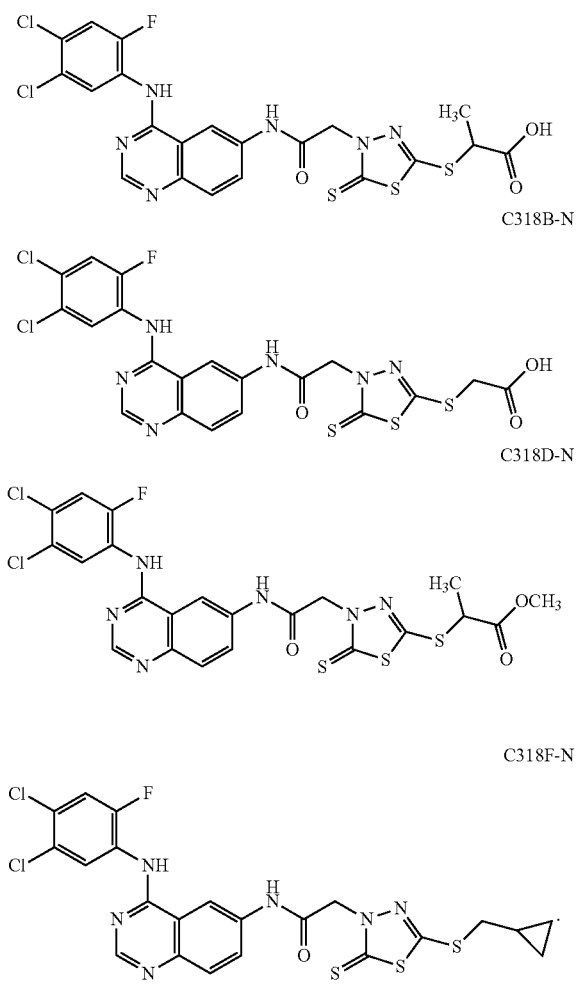

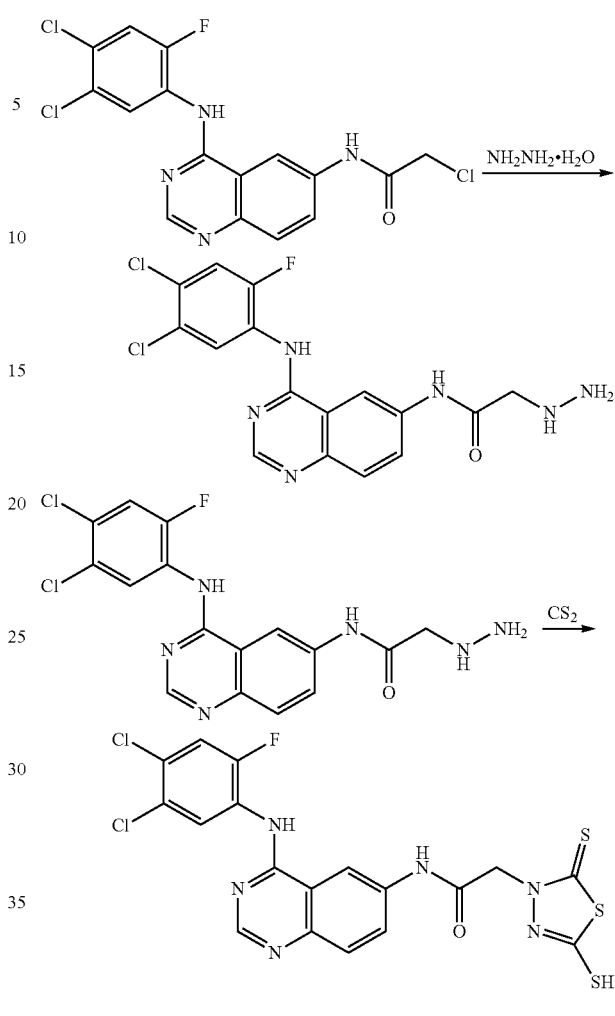

Accordingly, as used herein, reference to a compound as C318 may contain none, some, or all of a structural isomer having the structure identified as C318-N. Similarly, reference to a compound as C318A may contain none, some, or all of a compound having the structure identified as C318A-N; reference to a compound as C318B may contain none, some, or all of a compound having the structure identified as C318B-N; reference to a compound as C318D may contain none, some, or all of a compound having the structure identified as C318D-N; reference to a compound as C318F may contain none, some, or all of a compound having the structure identified as C318F-N; and reference to a compound as C300 may contain none, some, or all of a compound having the structure identified as C300-O.

Another scheme may also be used to prepare compounds containing the sulfanyl-3H[1,3,4]thiadiazole-2-thione moiety (for example, compounds of Formula (IA), which includes the compounds described as C318-N, C318A-N, C318B-N, C318D-N, and C318F-N), as exemplified below for the preparation of C318-N (see also see Example 2, below):

and the terminal thiol, —SH, can act as the nucleophile for further reaction using standardly available substrate reactants, e.g.,

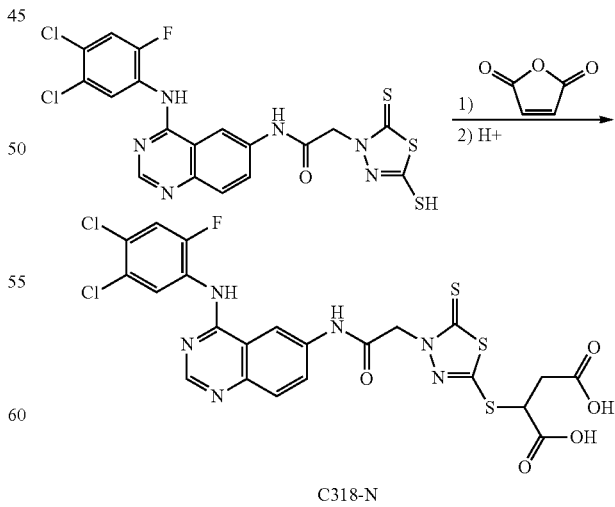

Formula (II) or Formula (IIA), then represents more generalized structures for the compounds described herein.

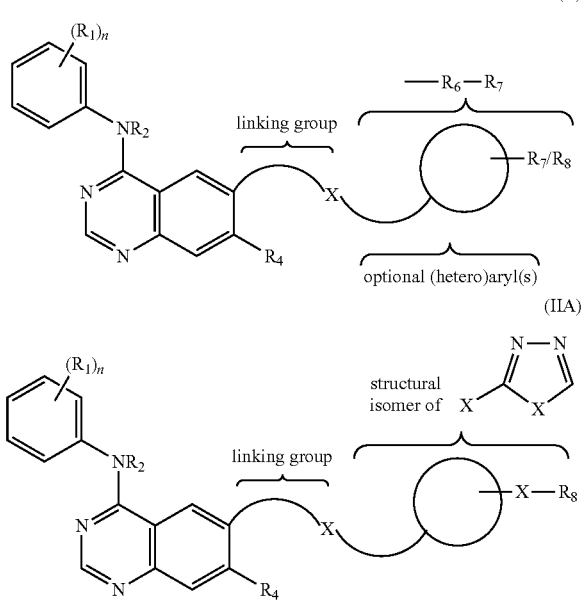

Pharmaceutical Compositions

As described above, the compounds described in the preceding section are useful for inhibiting a cell proliferative disorder characterized by over-activity and/or inappropriate activity of a receptor. Pharmaceutical compositions derived from each of the various embodied compounds described above are considered within the scope of this invention. Similarly, the use of any of the previously described compounds for the preparation of a medicament for the inhibition of a cell proliferative disorders characterized by over-activity and/or inappropriate activity of an epidermal growth factor receptor (EGFR), are considered to provide separate embodiments. In this regard, commercial packages comprising any of the pharmaceutical composition within the scope of this invention and a written matter associated therewith, the written matter stating that the pharmaceutical composition can or should be used for the prophylaxis and/or treatment of a disease caused by overexpression or aberrant activation of EGFR are also considered within the scope of this invention.

The invention contemplates those compositions wherein the compound exists as a pharmaceutically acceptable salts, as well as prodrugs and metabolites of these compounds.

The term "pharmaceutically acceptable salt" means those salts of compounds of the invention that are safe and effective for use in a subject and that possess the desired biological activity. Pharmaceutically acceptable salts include salts of acidic or basic groups present in compounds of the invention. Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

As the compounds of the invention may contain charged side chains or termini, they may be included in any of the above-described formulations as the free acids or bases or as pharmaceutically acceptable salts. Pharmaceutically acceptable salts are those salts which substantially retain the physiological activity of the free bases and which are prepared by reaction with inorganic acids. Pharmaceutical salts tend to be more soluble in aqueous and other protic solvents than are the corresponding free base forms. For a review on pharmaceutically acceptable salts see Berge et al., 66 J. Pharm. Sci 1-19 (1977), incorporated herein by reference.

Prodrugs and active metabolites of compounds disclosed herein are also within the scope of the invention. A prodrug is a pharmacologically inactive compound that is converted into a pharmacologically active agent by a metabolic transformation or any other chemical or biological process (e.g., hydrolysis). For example, in vivo, a prodrug can be acted on by naturally occurring enzyme(s) resulting in liberation of the pharmacologically active agent. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in "Design of Prodrugs," ed. H. Bundgaard, Elsevier, 1985, incorporated herein by reference.

An active metabolite is a compound that results from metabolism of another compound after administration of the latter to a subject. Metabolites can be identified by techniques well-known in the art.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds or a pharmaceutically acceptable salt thereof, are intimately admixed with a pharmaceutical carrier according to conventional pharmaceutical compounding techniques. The carrier may take a wide variety of forms depending on the form of preparation desired for administration.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Parenteral administration may comprise any suitable form of systemic delivery or delivery directly to the central nervous system. Administration may for example be intravenous, intra-arterial, intrathecal, intramuscular, subcutaneous, intra-muscular, intra-abdominal (e.g., intraperitoneal), etc., and may be effected by infusion pumps (external or implantable) or any other suitable means appropriate to the desired administration modality.

In preparing the compositions in oral dosage form, any of the usual pharmaceutical media may be employed. Thus, the compounds can be readily formulated by combining the compounds, salts, or analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

In some applications, it may be advantageous to utilize the active agent in a "vectorized" form, such as by encapsulation of the active agent in a liposome, micelle, or other encapsulant medium, or by fixation of the active agent, e.g., by covalent bonding, chelation, assembly, or associative coordination, on a suitable biomolecule, such as those selected from proteins, lipoproteins, glycoproteins, and polysaccharides.

For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For solid oral preparations such as, for example, powders, capsules, caplets, and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

For buccal administration, the compounds may take the form of tablets, lozenges, etc. formulated in conventional manner.

For topical administration the compounds of the invention may be formulated as solutions, gels, ointments, creams, suspensions, etc. as are well-known in the art.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Systemic formulations include those designed for administration by injection, e.g. subcutaneous, intravenous, intramuscular, intrathecal or intraperitoneal injection, as well as those designed for transdermal, transmucosal, oral or pulmonary administration.

Nasal and other mucosal spray formulations (e.g., inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

For administration by inhalation, the compounds for use according to the present invention are conveniently delivered in the form of an aerosol spray from pressurized packs or a nebulizer, with the use of a propellant acceptable as suitable by the pharmaceutical industry. Suitable propellants include, but are not limited to dichlorodifluoromethane, trichlorofluoromethane, dichlorotetrafluoroethane,1,1,1,2-tetrafluoroethane, P-227ea, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

The compounds may also be formulated in rectal or vaginal compositions such as suppositories or retention enemas, e.g., containing conventional suppository bases such as cocoa butter or other glycerides, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams and Wilkins: Philadelphia, Pa., 2000.

The formulation of the present invention can have immediate release, sustained release, delayed-onset release or any other release profile known to one skilled in the art.

The subject receiving the pharmaceutical composition is preferably an animal, more preferably a mammal, and most preferably a human.

The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages will normally fall within the range of from about 0.0025% to about 5%, more usually in the range of from about 0.005% to about 2%, more usually in the range of from about 0.05% to about 1%, and more usually in the range of form about 0.1% to about 0.5% by weight. These dosage ranges are intended to be indicative and are not intended to limit the scope of the invention in any way.

The amount of the active agent to be administered can typically range from between about 0.01 to about 25 mg/kg/day, preferably from between about 0.1 to about 10 mg/kg/day and most preferably from between about 0.2 to about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 25 to 200 mg of the compounds of the invention, and are preferably administered to a patient at a total daily dose of about 0.5 mg to about 2 g, preferably about 7.5 mg to about 750 mg, more preferably about 15 mg to 750 mg, and most preferably from about 50 to about 200 mg. As but one frame of reference, dose regimens of Tarceva® and Iressa® are listed in the Orange Book as in the range of 25 mg to 250 mg.

A pharmaceutical composition for parenteral administration contains from about 0.01% to about 100% by weight of the active agents of the present invention, based upon 100% weight of total pharmaceutical composition.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semi-permeable matrices of solid polymers containing the therapeutic agent. Several sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. Some preferred dosages range from 1 nM to 500 mM. Some preferred dosages range from 1 mM to 500 mM. Some preferred dosages range from 1 mg to 500 mg. Some preferred dosages range from 1000 mg to 3000 mg. Some preferred dosages range from 1500 mg to 2500 mg.

In cases of local administration or selective uptake, the effective local concentration of the compounds may not be related to plasma concentration. One having skill in the art will be able to optimize therapeutically effective local dosages without undue experimentation.

Inhibiting Cell Proliferative Disorders

Additionally, various embodiments provide methods of inhibiting a cell proliferative disorder, or treating a patient having a disease, characterized by over-activity and/or inappropriate activity of an EGFR, comprising administering to a patient in need of such treatment a pharmaceutically effective amount of any of the compounds described previously. In some embodiments, the treatment may be directed to over-activity and/or inappropriate activity of a wild type EGFR; in other embodiments, to a kinase mutated EGFR, for example, Tarceva®-resistant EGFR(L858R, T790M). Specific embodiments provide for methods of inhibiting a cell proliferative disorder or treating a patient by inhibiting a cell proliferative disorder within a patient wherein the cell proliferative disorder is cancer, especially for those cancers related to the over-activity and/or inappropriate activity of an EGFR, for example anal, breast, colon, prostate, lung, pancreas, ovary, or stomach cancer. More specific embodiment include those wherein the patient is a mammal, and even more specific embodiments include those wherein the patient is a human.

In treating a patient, the compounds of the present invention may be administered by themselves or in combinations with a pharmaceutically effective amount of an anti-cancer agent or performing a non-drug therapy or both to the patient. These anti-cancer agents may be administered at the same time, or at different times as part of an overall regimen of treatment. Non-drug therapy may include surgery, hypertensive chemotherapy, gene therapy, thermotherapy, cryotherapy, photodynamic therapy, laser cauterization and/or radiotherapy. The compounds of the present invention may be administered before or after (to prevent recurrence) any of these non-drug therapies. In one preferred embodiment, a patient having had a tumor associated with the cell proliferative disorder, wherein the tumor has been surgically removed, may be treated with a compound of the present invention to prevent recurrence or to inhibit metastasis of the disorder.

As used herein, the term therapeutic agent" is intended to mean a compound that, when present in a therapeutically effective amount, produces a desired therapeutic effect on a patient; for example, utilized to treat, combat, ameliorate, prevent or improve an unwanted condition or disease of a patient. Such inhibition may occur for example, and without limitation, via a direct interaction, and/or through a competitive interaction, or via an allosteric interaction with a corresponding receptor.

A "therapeutically effective amount" or "effective amount" of a composition is a predetermined amount calculated to achieve the desired effect. The activity contemplated by the present methods includes both medical therapeutic and/or prophylactic treatment, as appropriate. As used herein, "therapeutically effective amount" refers to the amount of active compound or pharmaceutical agent that elicits a biological or medicinal response in a tissue, system, animal, individual or human that is being sought by a researcher, veterinarian, medical doctor or other clinician, which includes one or more of the following as specified in the particular methodology: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reducing the severity of the pathology and/or symptomatology).

The term "prevent" as used herein to describe the action of inhibiting cell proliferation or the growth of tumors, or ameliorating the symptoms, prolonging the survival of, or otherwise mitigating the undesirable effects of the disease for which the patient is being treated.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response with or without excessive levels of side effects.

For detection of expression or activity of EGFR, a tissue (cancer tissue, blood vessel wall tissue, skin, oral mucosa etc.) or a body fluid (blood, lymph) and the like, which is obtained from patients, is applied to a test to detect expression or activity of EGFR. Such tests are known to those skilled in the art. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

As mentioned above, the compounds of the present invention are effective in the treatment of cancer patients and also expected to be an agent for the prophylaxis and/or treatment of preventing transition from hormone sensitive cancer to resistant cancer in prostate cancer and breast cancer. Moreover, it is expected to an agent for the prophylaxis and/or treatment of angiogenesis associated with the growth of solid cancer and sarcoma, angiogenesis associated with cancer metastasis, angiogenesis associated with diabetic retinopathy, arteriosclerosis, psoriasis and the like.

The "overexpression or activation of EGFR" is an expression or activity not less than the expression amount or activity necessary for homeostasis of living organisms, and the expression or activity not less than the expression amount or activity necessary for normal tissue of the same origin.

The "patients showing overexpression or activation of EGFR" means the patients wherein EGFR is excessively expressed or activated, and preferably the patients wherein both are excessively expressed or activated. The EGFR inhibitor of the present invention is characterized by administration for the treatment of patients, wherein EGFR is excessively expressed or activated as mentioned above.

The "EGFR inhibitor" of the present invention is preferably an EGFR inhibitor to be administered to patients wherein EGFR is excessively expressed or activated. It is possible to use an EGFR inhibitor and another form of treatment simultaneously, separately or at time intervals. In other words, it is possible to administer an EGFR inhibitor and another drug or form of treatment simultaneously, separately or, for example, in a staggered manner in a single day or at given time intervals for several days to several weeks or several months, by various different routes.

The amount of compound administered will, of course, be dependent on the subject being treated, on the subject's weight, the severity of the affliction, the manner of administration and the judgment of the prescribing physician. However, to the extent that these compounds provide improved activity relative to other known small molecules in in vivo, in vitro, and animal studies, in the broadest sense, recommended dosages are those similar to those currently prescribed for other small molecules for this same purpose.

The therapy may be repeated intermittently while symptoms detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use human. The dosage of the compounds described lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1). Preferred dosages range from 1 nM to 500 mM.

EXAMPLES

Example 1

Sources of the Materials

Acetone and potassium carbonate were purchased from Sigma-Aldrich, catalog numbers #270725 and #209619, respectively.

EGFR "Inhibitor 3" was purchased from Calbiochem, catalog #324833.

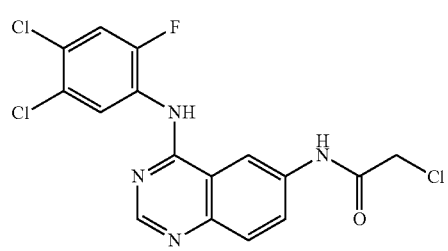

Inhibitor 3

The thiol starting materials were purchased according to:
2-Mercaptoethanol (2-ME): SIGMA #M3148;

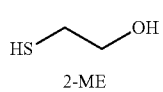

2-ME

EES5: Maybridge #SPB02607SC;

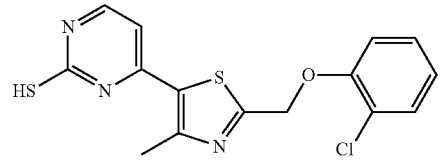

EES5

EES18: Maybridge #BTB12608SC;

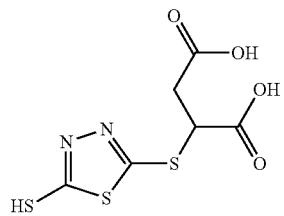

EES18

EES18A: Oakwood Products #60725-23-7;

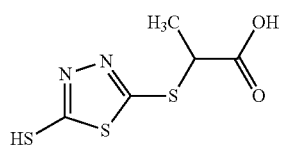

EES18A

EES18B: Enamine #T5878273;

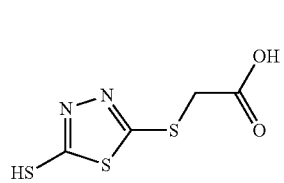

EES18B

EES18D: Otava Chemicals #7212920033; and

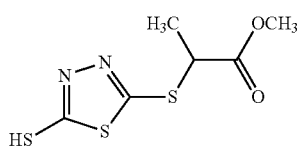

EES18D

EES18F: Maybridge #TL00159ZZ

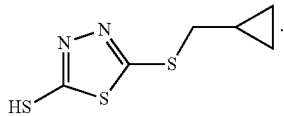

EES18F

Example 2

Syntheses of Compounds

Several embodiments of the present invention have been synthesized by reacting the chloroacetamide group of a model tyrosine kinase inhibitor molecule with the thiol group of several mutation-mimicking compounds. While not intending to limit the scope of the invention, these syntheses provide one way of producing these certain, and a wider range of, embodiments.

In separate syntheses, 2 mg of the EES compound was mixed with 1 mg of Inhibitor 3 in 1 mL dry acetone (with 15 mg anhydrous potassium carbonate) and allowed to incubate for 1 hour or overnight at room temperature. The reaction mixture was loaded onto a C4 reverse phase Beckman Ultrasphere® C18 Semi-Prep HPLC Column (P/N 235328) using an acetonitrile (98%)/TFA (0.1%) and double distilled water/TFA (0.1%) solvent system for further purification. In each case, the Mass Spectrometry Center, Department of Chemistry, University of Pennsylvania confirmed the identity of the target molecule.

This method was used to prepare compounds identified as C53, C300, C318, C318A, C318B, C318D, and C318F, according to the schemes described above.

An alternative scheme for producing the nitrogen linked cogeners of C318, C318A, C318B, C318D, and C318F (i.e., to produce C318-N, C318A-N, C318B-N, C318D-N, and C318F-N) is also provided below (exemplified for C318N):

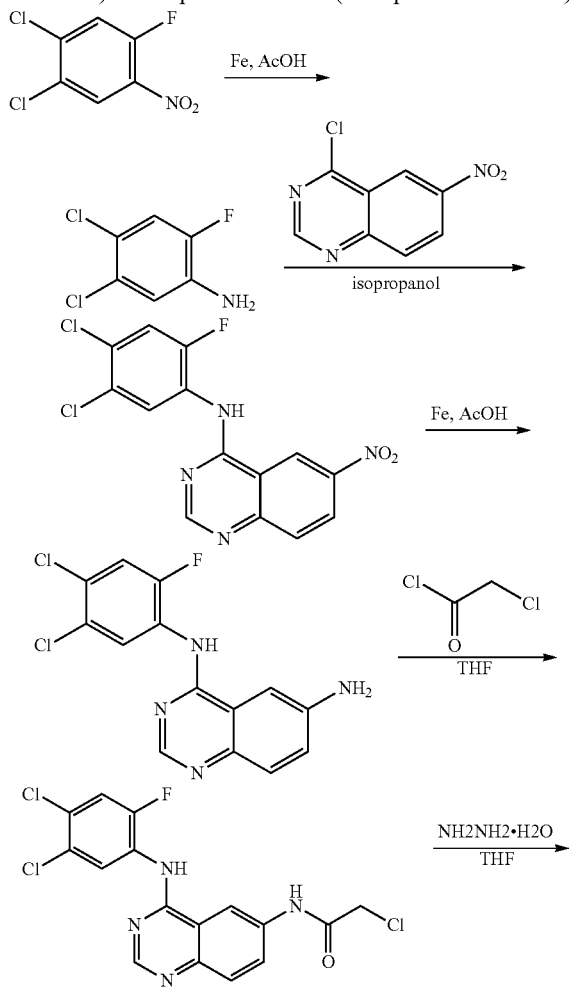

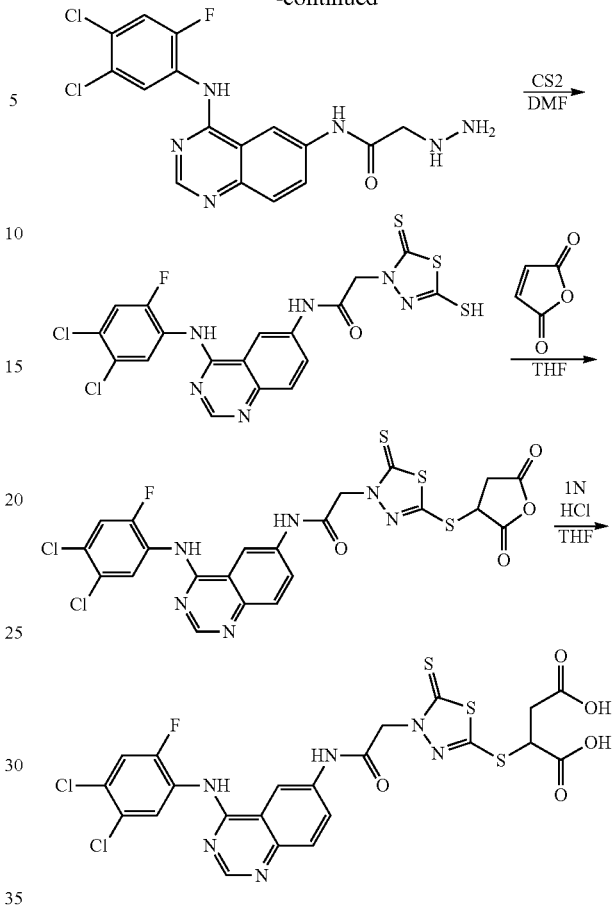

The conditions for the individual transformations are provided below.

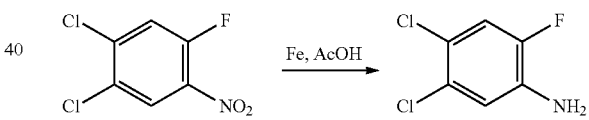

Into a 100-mL 3-necked round-bottom flask purged and maintained with an inert atmosphere of nitrogen, was placed Fe (14 g, 250.00 mmol, 10.50 equiv), AcOH (1.5 mL), water (24 mL). This was followed by the addition of 1,2-dichloro-4-fluoro-5-nitrobenzene (5 g, 23.81 mmol, 1.00 equiv) at 100° C. The resulting solution was stirred for 30 min at 100° C. The reaction mixture was cooled to 10° C. with a water/ice bath. The pH value of the solution was adjusted to 8-9 with saturated aqueous sodium bicarbonate. The solids were filtered out. The resulting solution was extracted with 3×40 mL of ether and the organic layers combined and dried over anhydrous sodium sulfate and concentrated under vacuum. This resulted in 4.2 g (98%) of 4,5-dichloro-2-fluoroaniline as a white solid.

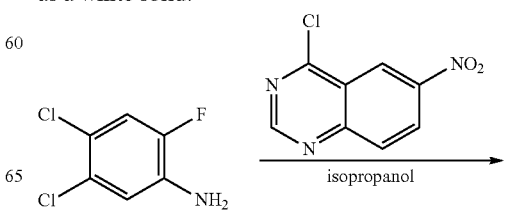

-continued

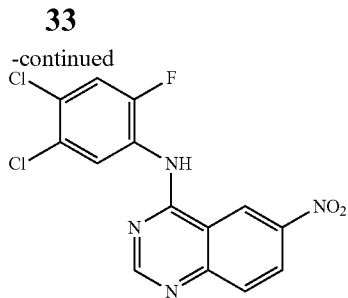

Into a 50-mL 3-necked round-bottom flask purged and maintained with an inert atmosphere of nitrogen, was placed 4,5-dichloro-2-fluoroaniline (3.6 g, 20.00 mmol, 1.20 equiv), 4-chloro-6-nitroquinazoline (3.1 g, 14.79 mmol, 1.00 equiv), i-propanol (100 mL). The resulting solution was stirred for 2 h at 90° C. The reaction mixture was cooled to room temperature. The solids were collected by filtration. The filter cake was washed with 3×20 mL of i-PrOH. This resulted in 5.4 g (99%) of N-(4,5-dichloro-2-fluorophenyl)-6-nitroquinazolin-4-amine as a light yellow solid.

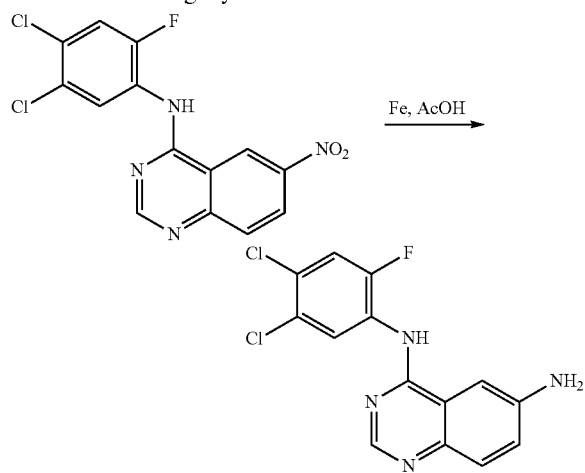

Into a 250-mL 3-necked round-bottom flask, was placed ethanol (10 mL), water (60 mL), Fe (9 g, 10.50 equiv), AcOH (1.5 mL). This was followed by the addition of N-(4,5-dichloro-2-fluorophenyl)-6-nitroquinazolin-4-amine (5.4 g, 15.29 mmol, 1.00 equiv) at 100° C. The resulting solution was stirred for 1.5 h at 100° C. The reaction mixture was cooled to 10° C. The pH value of the solution was adjusted to 8-9 with saturated aqueous sodium bicarbonate. The resulting solution was extracted with 3×50 mL of ethyl acetate and the organic layers combined and dried over anhydrous sodium sulfate and concentrated under vacuum. This resulted in 4.5 g (91%) of 4-N-(4,5-dichloro-2-fluorophenyl)quinazoline-4,6-diamine as a light yellow solid.

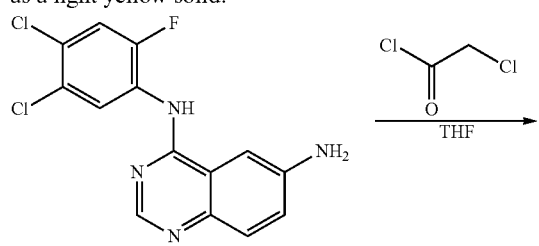

-continued

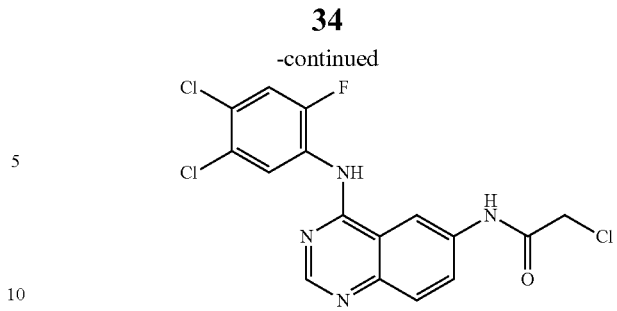

Into a 100-mL 3-necked round-bottom flask purged and maintained with an inert atmosphere of nitrogen, was placed 4-N-(4,5-dichloro-2-fluorophenyl)quinazoline-4,6-diamine (1.6 g, 4.95 mmol, 1.00 equiv), tetrahydrofuran (30 mL). This was followed by the addition of 2-chloroacetyl chloride (0.47 mL, 1.20 equiv) dropwise with stirring at 0° C. The resulting solution was stirred for 30 min at 0° C. The pH value of the solution was adjusted to 8 with saturated aqueous sodium bicarbonate. The resulting solution was extracted with 3×30 mL of ethyl acetate and the organic layers combined and dried over anhydrous sodium sulfate and concentrated under vacuum. This resulted in 1.8 g (91%) of 2-chloro-N-[4-[(4,5-dichloro-2-fluorophenyl)amino]quinazolin-6-yl]acetamide as a yellow solid.

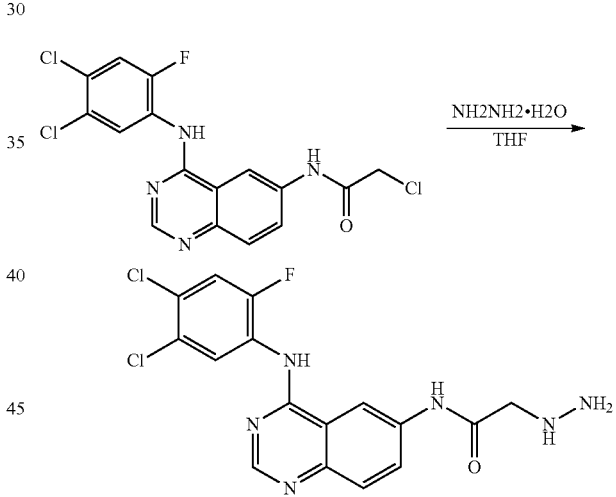

Into a 100-mL 3-necked round-bottom flask, was placed NH$_2$NH$_2$.H$_2$O (300 mg, 6.00 mmol, 3.00 equiv), tetrahydrofuran (10 mL). This was followed by the addition of a solution of 2-chloro-N-[4-[(4,5-dichloro-2-fluorophenyl)amino] quinazolin-6-yl]acetamide (600 mg, 1.50 mmol, 1.00 equiv) in THF (10 mL). The resulting solution was stirred overnight at room temperature. The reaction was then quenched by the addition of 20 mL of water. The resulting solution was extracted with 3×20 mL of ethyl acetate and the organic layers combined and dried over anhydrous sodium sulfate and concentrated under vacuum. This resulted in 620 mg (98%) of N-[4-[(4,5-dichloro-2-fluorophenyl)amino]quinazolin-6-yl]-2-hydrazinylacetamide as a light yellow solid.

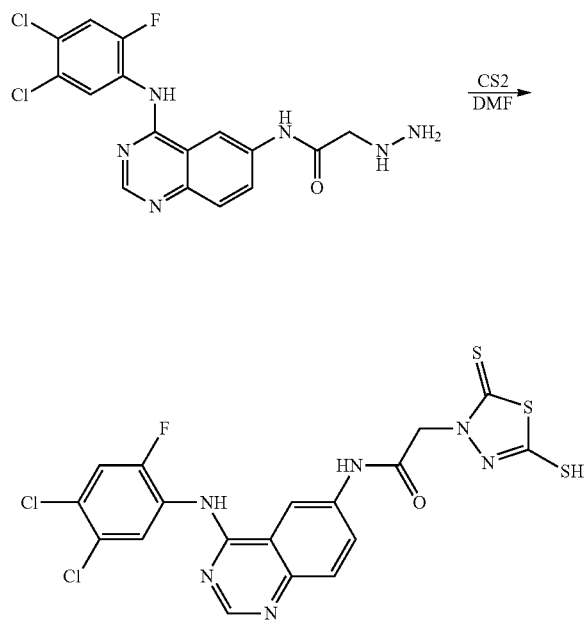

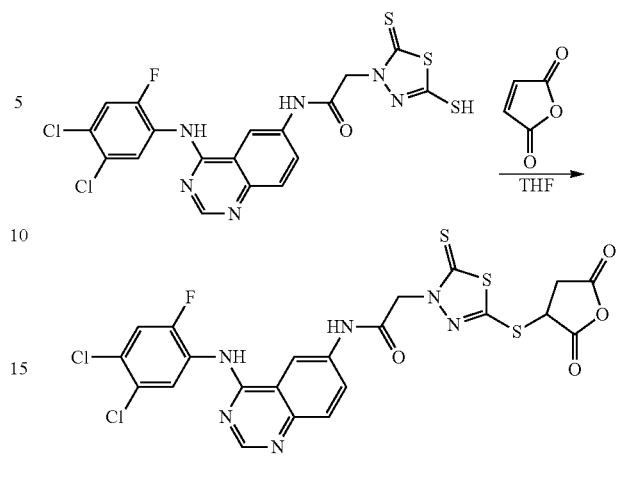

Into a 100-mL 3-necked round-bottom flask, was placed N-[4-[(4,5-dichloro-2-fluorophenyl)amino]quinazolin-6-yl]-2-hydrazinylacetamide (600 mg, 1.52 mmol, 1.00 equiv), N,N-dimethylformamide (20 mL), pyridine (0.3 mL), CS₂ (0.3 mL). The resulting solution was stirred for 1.5 h at 100° C. The pH value of the solution was adjusted to 7 with AcOH. The resulting solution was diluted with 100 mL of water. The solids were collected by filtration. The filter cake was washed with 2×20 mL of water. The crude product was purified by Prep-HPLC. This resulted in 300 mg (38%) of N-[4-[(4,5-dichloro-2-fluorophenyl)amino]quinazolin-6-yl]-2-(5-sulfanyl-2-sulfanylidene-2,3-dihydro-1,3,4-thiadiazol-3-yl)acetamide as a yellow solid.

Into a 50-mL round-bottom flask, was placed N-[4-[(4,5-dichloro-2-fluorophenyl)amino]quinazolin-6-yl]-2-(5-sulfanyl-2-sulfanylidene-2,3-dihydro-1,3,4-thiadiazol-3-yl)acetamide (150 mg, 0.29 mmol, 1.00 equiv), 2,5-dihydrofuran-2,5-dione (28 mg, 0.29 mmol, 1.00 equiv), tetrahydrofuran (10 mL). The resulting solution was stirred for 4 h at 70° C. The resulting mixture was concentrated under vacuum. This resulted in 140 mg (78%) of N-[4-[(4,5-dichloro-2-fluorophenyl)amino]quinazolin-6-yl]-2-[5-[(2,5-dioxooxolan-3-yl)sulfanyl]-2-sulfanylidene-2,3-dihydro-1,3,4-thiadiazol-3-yl]acetamide as a brown solid.

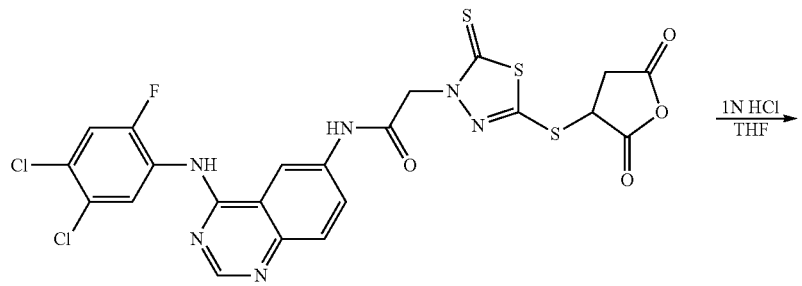

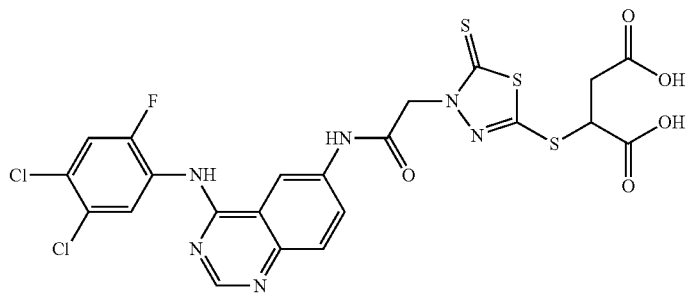 [SMILES: O=C(O)CC(Sc1nn(CC(=O)Nc2ccc3ncnc(Nc4cc(Cl)c(Cl)cc4F)c3c2)c(=S)s1)C(=O)O]

Into a 50-mL round-bottom flask, was placed N-[4-[(4,5-dichloro-2-fluorophenyl)amino]quinazolin-6-yl]-2-[5-[(2,5-dioxooxolan-3-yl)sulfanyl]-2-sulfanylidene-2,3-dihydro-1,3,4-thiadiazol-3-yl]acetamide (200 mg, 0.33 mmol, 1.00 equiv), tetrahydrofuran (10 mL), hydrogen chloride (1 N) (12 mL). The resulting solution was stirred for 30 min at 25° C. The resulting mixture was concentrated under vacuum. The crude product was purified by Prep-HPLC (Table 1). This resulted in 58 mg (28%) of 2-([4-[([4-[(4,5-dichloro-2-fluorophenyl)amino]quinazolin-6-yl]carbamoyl)methyl]-5-sulfanylidene-4,5-dihydro-1,3,4-thiadiazol-2-yl]sulfanyl)butanedioic acid as a brown solid.

LC-MS: (ES, m/z): 629 [M+H]$^+$

H-NMR (300 MHz) (DMSO, ppm): δ2.730-2.959 (2H, m), 4.394-4.435 (1H, m), 5.264 (2H, s), 7.796 (4H, s), 8.458 (1H, s), 8.782 (1H, s), 10.056 (1H, s), 10.796 (1H, s).

TABLE 1

Instrument Name: Shimadzu LCMS-2020

<<Pump>>

| Mode | Binary gradient |
|---|---|
| Total Flow | 1.000 mL/min |

<<Mobile Phase>>

| Comment | Phase A: water (0.1% FA) |
|---|---|
| | Phase B: ACN (0.1% FA) |

<<LC Time Program>>

| Time | Module | Command | Value |
|---|---|---|---|
| 0.01 | Pumps | Pump B Conc. | 5 |
| 6.00 | Pumps | Pump B Conc. | 70 |
| 7.00 | Pumps | Pump B Conc. | 70 |
| 7.10 | Pumps | Pump B Conc. | 5 |
| 7.70 | Controller | Stop | |

<<Column Information>>

| Column Name | Shimadzu shim-pack XR-ODS |
|---|---|
| Column ID | 00132755 |
| Column Length | 50 mm |
| Inner Diameter | 3.0 mm |
| Description | partical size: 2.2 μm |

<<Interface>>

| Interface | ESI |
|---|---|
| DL Temperature | 250 C. |
| Nebulizing Gas Flow | 1.50 L/min |
| Heat Block | 250 C. |
| Drying Gas | On |
| | 6.00 L/min |

Example 3

NE91 cells (mouse fibroblasts over-expressing wild type human type EGFR) were starved overnight, incubated with an exemplary mutation mimicking compound (designated EEO3, see below; 0.1 μM; lanes 2, 6 of FIG. 2), Tarceva® (0.1 μM; lanes 3, 7 of FIG. 2), or both (lanes 4, 8 of FIG. 2) for one hour, and harvested (lanes 1-4 of FIG. 2), or induced with EGF (50 ng/mL) for 15 minutes and harvested. Equal amounts of total protein were loaded on 10% SDS-PAGE gel, separated, transferred to a PVDF membrane, and probed with pY99, pERK antibodies (Santa Cruz Biotechnology), or antibodies against specific phosphotyrosines of EGFR (pY845, pY1068, pY992) or AKT phosphor-serine (473; Cell Signaling Technology). Total EGFR and γ-tubulin levels were determined as controls using the 1005 (Santa Cruz Biotechnology) and GTU88 (Sigma) Abs, respectively. The resulting data are presented in FIG. 2.

Studies described in U.S. Patent Application Ser. No. 61/453,626, filed Mar. 17, 2011, have shown that certain mutation mimicking compounds (MMCs) can reproduce some important features of the mutant receptors including constitutive phosphorylation of total EGFR, enhanced constitutive phosphorylation of specific Tyr residues, and enhanced susceptibility of the downstream AKT and ERK signaling to inhibition by Tarceva®. EEO3 is one designation used in that co-pending application for the following structure:

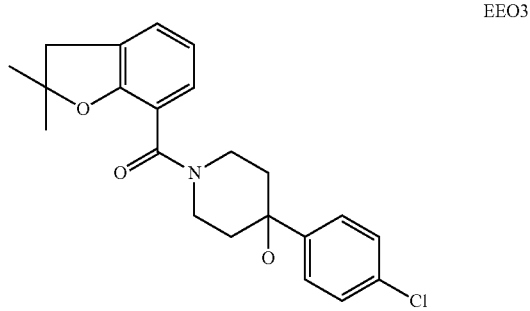 [SMILES: CC1(C)Cc2cccc(C(=O)N3CCC(O)(c4ccc(Cl)cc4)CC3)c2O1]

EEO3

Representative results are given in FIG. 2. The L858 mutation is known to result in enhanced constitutive phosphorylation of total EGFR as well as enhanced constitutive phosphorylation of Tyr 845 and Tyr 1068, but to have no effect on constitutive phosphorylation of Tyr 992. See Sordella R, et al, Gefitinib-Sensitizing EGFR Mutations in Lung Cancer Activate Anti-Apoptotic Pathways. Science 20 Aug. 2004: Vol. 305 no. 5687 pp. 1163-1167 DOI: 10.1126/science.1101637, which is incorporated by reference in its entirety. The compounds of the present invention show these features; i.e., enhance constitutive phosphorylation of total EGFR (similar to that shown in upper panel of FIG. 2) and of Tyr 845 (similar to that shown in panel 2 from the top in FIG. 2) and Tyr 1068 (similar to that shown in panel 3 from the top in FIG. 2), but to have no effect on constitutive phosphorylation of Tyr 992 (similar to that shown in panel 4 from the top in FIG. 2). Also similar to the effects produced by the mutations, the compounds enhance Tarceva®-induced inhibition of phosphorylation of total EGFR (similar to that shown in upper panel in FIG. 2), of Tyr 845 (similar to that shown in panel 2 from the top in FIG. 2), of TYR 1068 (similar to that shown in panel 3 from the top on FIG. 2), and are expected to enhance the downstream signaling molecules including AKT (similar to that shown in panel 5 from the top in FIG. 2) and ERK (as shown in panel 6 from the top in FIG. 2).

Example 4

Figure 3:
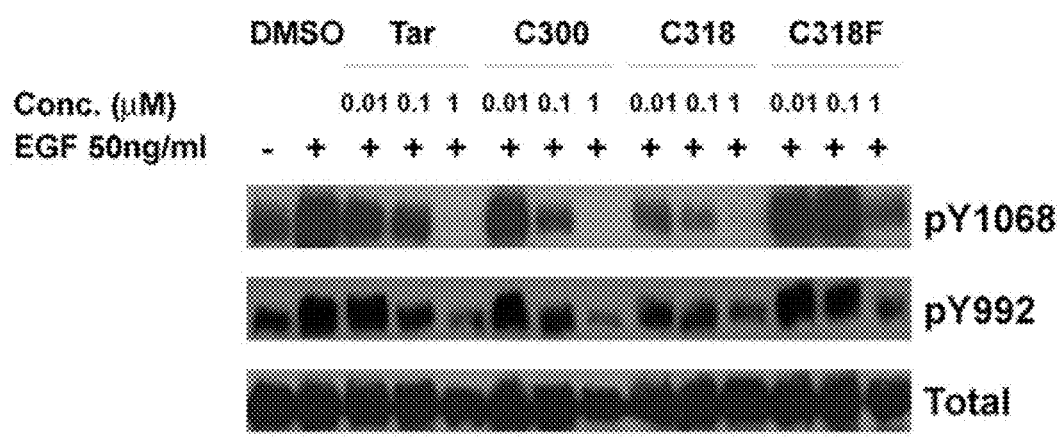
FIG. 3 illustrates the effect of various several embodiments of the invention, compared with Tarceva® on the phosphorylation of Tyr 1068 and Tyr 992 of EGFR kinase (Example 4).
Figure 6:
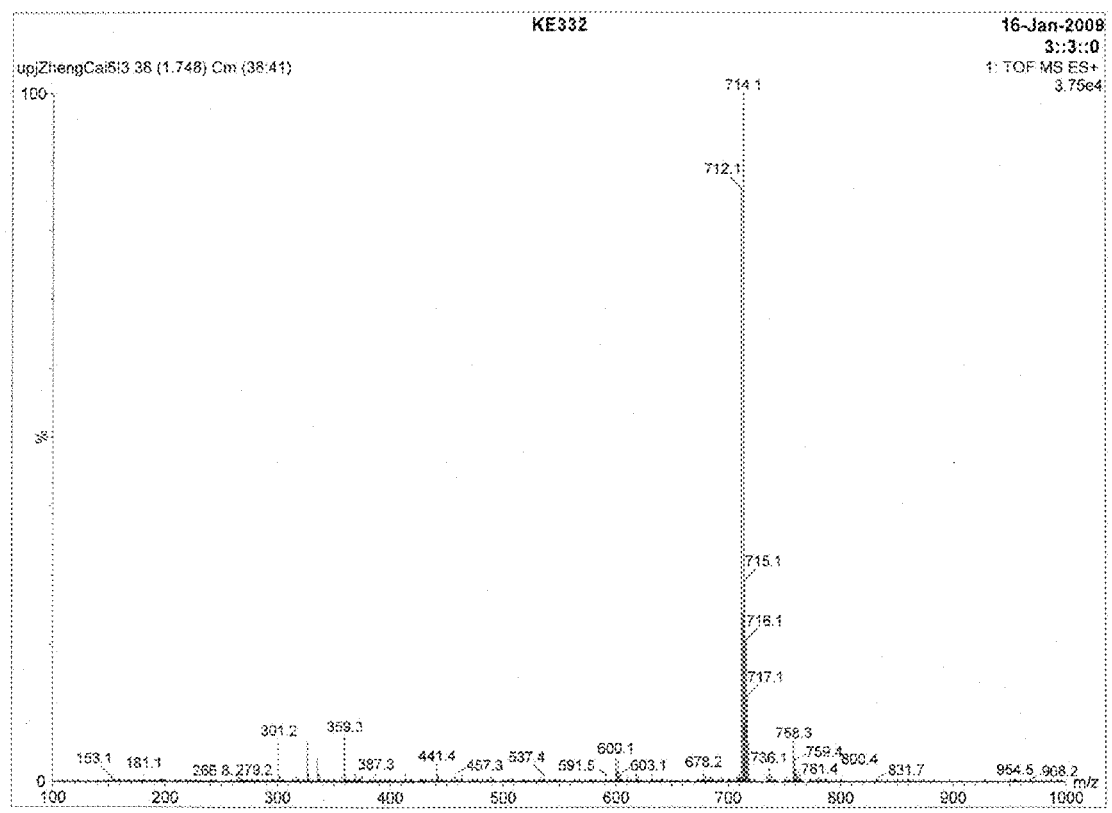
FIG. 6 provides mass spectral data for several embodiments described herein.

To estimate the inhibitory activity of Compound C318 on EGFR signaling, its effect on the phosphorylation of specific Tyr residues of EGFR kinase was tested (see FIG. 3). The methods used were the same as described in Example 3.

Consistent with the data obtained with the mutation mimicking compound, EEO3 (see above), Compound C318 showed a stronger activity than Tarceva® in inhibition of Tyr 1068, but not Tyr 992. The inhibitory effects of C300 and C-318F are not as strong as that of C-318, possibly because their binding affinity is lower. This result agrees with the proposed dual mechanism of action for this molecule; i.e., that one part of the molecule acts as a traditional tyrosine kinase inhibitor, while the other part acts as a mutation mimicking compound by restraining the kinase domain in an activated conformation.

Example 5

To evaluate the inhibitory effect of C318 on cell proliferation in vitro, the compound was tested for inhibition of the anchorage independent growth of EGFR-over-expressing NE91 cells (FIG. 4). Anchorage independent growth was determined by assessing the colony-forming efficiency of cells suspended in soft agar. Cells (5×10³) were suspended in a 1 ml top layer (0.375% agarose 10% FBS/DMEM) in 6-cm culture dishes containing a 3 ml cell-free feeder layer consisting of 0.5% agarose in DMEM supplemented with 10% FBS and 20 mM Hepes (pH 7.5). Culture dishes were fed by 0.7 ml 10% FBS/DMEM containing 0.1 uM of C318 or Tarceva® once every 5 days. Colonies were visualized and counted after 3 weeks after staining with p-iodonitrotetrazolium violet (1 mg/ml).

At 0.1 µM concentration, C318 was more active than Tarceva® in inhibiting anchorage independent growth in the EGFR over-expressing cell line NE91. See FIG. 4(D).

Example 6

In an additional set of tests, EGFR assays were done to determine IC50 values using HotSpot$^{SM}$ technology with the peptide substrate poly[Glu:Tyr] (4:1, 0.2 mg/ml). These tests were conducted by Reaction Biology Corp. (Malvern, Pa.; http://www.reactionbiology.com). Kinase reactions were carried out in 20 mmol/L HEPES (pH 7.5), 10 mmol/L MgCl2, 1 mmol/L EGTA, 0.02% Brij 35, 0.02 mg/mL bovine serum albumin, 2 mmol/L DTT, and 1% DMSO. The final concentration of ATP was 10 µmol/L. Purified recombinant kinases were incubated with serial 3-fold dilutions of test compounds starting at a final concentration of 1 µmol/L. ATP concentration was 10 µmol/L. Dose response curves were fitted using Prism 5.0 from Graph-Pad Software.

Figure 7:
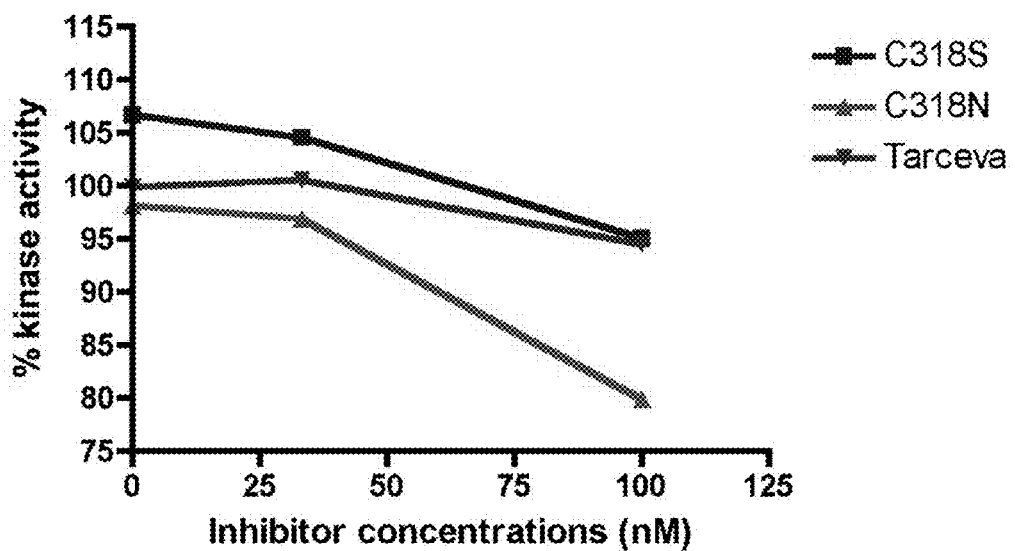
FIG. 7 provides in vitro kinase activity data for EGFR kinase mutant EGFR (L858R, T790M) as described in Example 6.

Both C318 and C318N exhibited IC50s comparable to Tarceva® (0.5-1 nM). All these inhibitors were also tested by the same kinase assay using the Tarceva®-resistant EGFR kinase mutant, EGFR (L858R, T790M). As shown in FIG. 7, C318N has better activity than C318 (data in FIG. 7 derived from C318 is labeled as C318S) and Tarceva® to inhibit the activity of this kinase. At 100 nM, C318 exhibited about the same inhibition as Tarceva®. Under the same conditions, C318N showed about 20% inhibition of EGFR(L858R, T790M), outperforming both Tarceva® and C318/C318S in this test.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, in their entirety.

What is claimed:

1. A compound having a structure of Formula I:

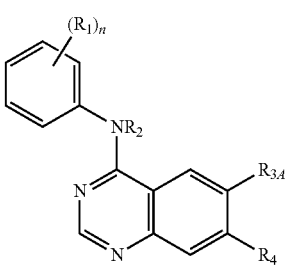

(I)

wherein $R_1$ is independently H, optionally substituted amino, optionally substituted $C_{1-6}$ alkyl, optionally substituted $C_{1-6}$ alkoxy, optionally substituted $C_{1-6}$ alkenyl, optionally substituted $C_{1-6}$ alkynyl, optionally substituted benzyloxy, cyano, halo, hydroxy, nitro, optionally substituted phenoxy, or mono-, di-, or trifluoromethyl;

n is 1, 2, or 3;

$R_2$ is independently H or $C_{1-3}$-alkyl;

$R_{3A}$ is —$OR_{5A}$, —$NR_2R_{5A}$, —$SR_{5A}$, —$C(O)R_{5A}$, —$C(O)OR_{5A}$, —$C(O)N(R_2)(R_{5A})$, —$OC(O)R_{5A}$, —$OC(O)OR_{5A}$, —$OC(O)NR_2R_{5A}$, —$NR_2C(O)R_{5A}$, —$NR_2C(O)OR_{5A}$;

$R_4$ is H, —$N(R_2)_2$, optionally substituted $C_{1-3}$-alkyl, optionally substituted $C_{1-3}$-alkoxy, cyano, halo, hydroxy, nitro, or mono-, di-, or trifluoromethyl;

$R_{5A}$ is —($C_{1-4}$-alkyl)-X—$R_6$—$R_7$;

X is O, S, or $N(R_2)$;

$R_6$ is a bond;

$R_7$ is either (i) a $C_{1-4}$-alkyl substituted by at least one —OH or —$C(O)OR_2$ or —$C(O)N(R_2)_2$, or (ii) a heteroaryl having 5 ring members, containing 1-3 heteroatoms and substituted by $R_2$ and —X—$R_8$; and $R_8$ is $C_{1-3}$ alkyl substituted by at least one —OH, —COOH, —$C(O)O$—$C_{1-4}$ alkyl, —$C(O)N(R_2)_2$, or $C_{1-5}$ cycloalkyl;

or a pharmaceutically acceptable salt form thereof.

2. A compound that is a product of reaction between a compound of Formula III and a compound of Formula IV:

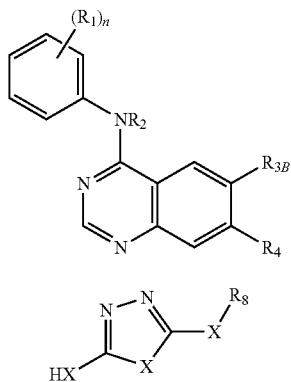

(III)

(IV)

wherein
R$_1$ is independently H, optionally substituted amino, optionally substituted C$_{1-6}$ alkyl, optionally substituted C$_{1-6}$ alkoxy, optionally substituted C$_{1-6}$ alkenyl, optionally substituted C$_{1-6}$ alkynyl, optionally substituted benzyloxy, cyano, halo, hydroxy, nitro, optionally substituted phenoxy, or mono-, di-, or trifluoromethyl;

n is 1, 2, or 3;

R$_2$ is independently H or C$_{1-3}$-alkyl;

R$_{3B}$ is —OR$_{5B}$, —NR$_2$R$_{5B}$, —SR$_{5B}$, —C(O)R$_{5B}$, —C(O)OR$_{5B}$, —C(O)N(R$_2$)(R$_{5B}$), —OC(O)R$_{5B}$, —OC(O)OR$_{5B}$, —OC(O)NR$_2$R$_{5B}$, —NR$_2$C(O)R$_{5B}$, —NR$_2$C(O)OR$_{5B}$;

R$_4$ is H, —N(R$_2$)$_2$, optionally substituted C$_{1-3}$-alkyl, optionally substituted C$_{1-3}$-alkoxy, cyano, halo, hydroxy, nitro, or mono-, di-, or trifluoromethyl;

R$_{5B}$ is —(C$_{0-4}$-alkyl)-L, where L is a leaving group;

X is independently at each occurrence O, S, or N(R$_2$);

R$_8$ is C$_{1-3}$ alkyl substituted by at least one —OH, —COOH, —C(O)O—C$_{1-4}$ alkyl, —C(O)N(R$_2$)$_2$, or C$_{3-5}$ cycloalkyl;

or a pharmaceutically acceptable salt form thereof.

3. The compound of claim 2, wherein each R$_1$ is independently H, optionally substituted C$_{2-6}$ alkynyl, optionally substituted benzyloxy, or halo.

4. The compound of claim 2, wherein each R$_1$ is independently Cl or F.

5. The compound of claim 2, wherein R$_2$ is H.

6. The compound of claim 1 wherein R$_{3A}$ is —NR$_2$C(O)R$_{5A}$.

7. The compound of claim 2 wherein R$_{3B}$ is —NR$_2$C(O)R$_{5B}$.

8. The compound of claim 2, wherein R$_4$ is H.

9. The compound of claim 1 wherein R$_{5A}$ is —CH$_2$—S—R$_6$—R$_7$.

10. The compound of claim 1 wherein R$_{5B}$ is —CH$_2$—Cl.

11. The compound of claim 1 wherein R$_1$ is ethynyl, n is 1, R$_2$ is H, R$_{3A}$ is —NR$_2$C(O)R$_{5A}$, R$_4$ is H, and R$_{5A}$ is —CH$_2$—S—R$_6$—R$_7$.

12. The compound of claim 2 wherein R$_1$ is ethynyl, n is 1, R$_2$ is H, R$_{3B}$ is —NR$_2$C(O)R$_{5B}$, R$_4$ is H, and R$_{5B}$ is —CH$_2$—Cl.

13. The compound of claim 1, wherein each R$_{1q}$ is independently Cl or F, R$_2$ is H, R$_{3A}$ is —NR$_2$C(O)R$_{5A}$, R$_4$ is H, and R$_{5A}$ is —CH$_2$—S—R$_6$—R$_7$.

14. The compound of claim 2 wherein each R$_1$ is independently Cl or F, R$_2$ is H, R$_{3B}$ is —NR$_2$C(O)R$_{5B}$, R$_4$ is H, and R$_{5B}$ is —CH$_2$—Cl.

15. The compound of claim 1, wherein R$_6$ is a bond and R$_7$ is a C$_{1-4}$-alkyl substituted by at least one —OH or —COOH.

16. The compound of claim 15 wherein R$_6$ is a bond and R$_7$ is a CH$_2$CH$_2$OH or CH$_2$CH$_2$COOH.

17. The compound of claim 1, wherein R$_6$ is a bond and R$_7$ is a heteroaryl having 5 ring members containing 1-3 heteroatoms and substituted by R$_2$ and —X—R$_8$.

18. The compound of claim 2, wherein X is S.

19. The compound of claim 1, wherein R$_8$ is —CH$_2$COOR$_2$, —CH(CH$_3$)COOR$_2$, or —CH$_2$-cC$_3$H$_7$.

20. The compound of claim 2 wherein the compound of Formula IV is:

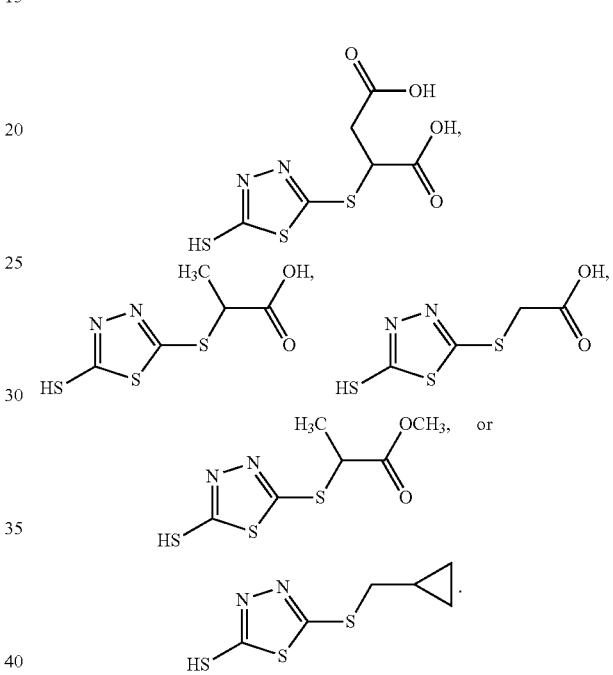

21. The compound of claim 1, having a structure:

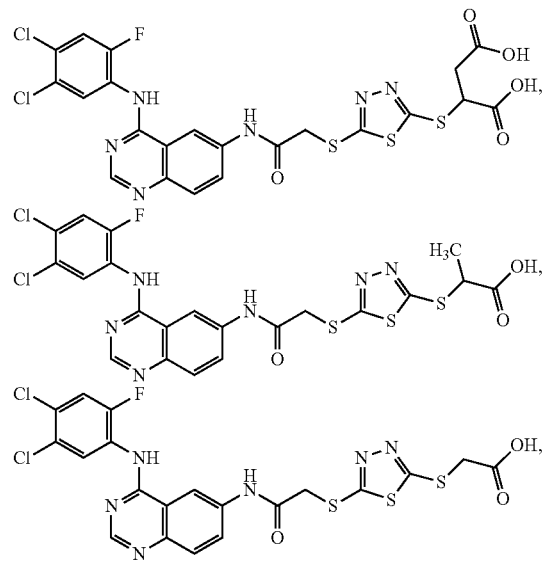

-continued

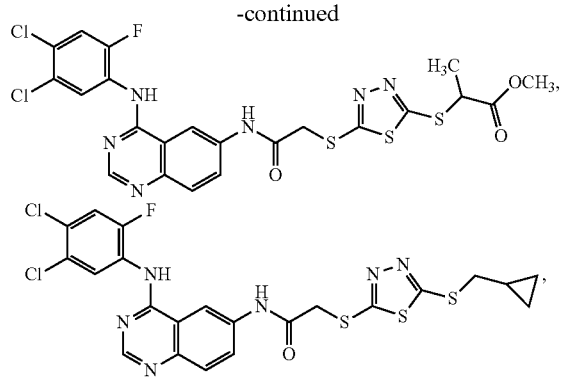

or a pharmaceutically acceptable salt thereof.

22. A pharmaceutical composition comprising a compound of claim 1 and a pharmaceutically acceptable excipient, suitable for administration to a human patient.

23. A compound having a structure of Formula (IA):

(IA)

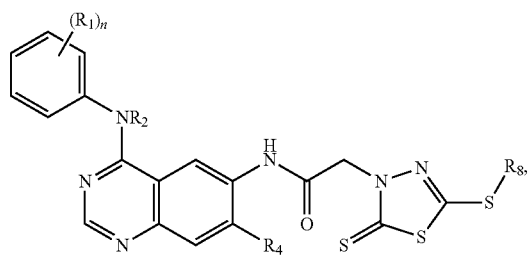

wherein:
- $R_1$ is independently H, optionally substituted amino, optionally substituted $C_{1-6}$ alkyl, optionally substituted $C_{1-6}$ alkoxy, optionally substituted $C_{1-6}$ alkenyl, optionally substituted $C_{1-6}$ alkynyl, optionally substituted benzyloxy, cyano, halo, hydroxy, nitro, optionally substituted phenoxy, or mono-, di-, or trifluoromethyl;
- n is 1, 2, or 3;
- $R_2$ is independently H or $C_{1-3}$-alkyl;
- $R_4$ is H, —N$(R_2)_2$, optionally substituted $C_{1-3}$-alkyl, optionally substituted $C_{1-3}$-alkoxy, cyano, halo, hydroxy, nitro, or mono-, di-, or trifluoromethyl; and
- $R_8$ is $C_{1-3}$ alkyl substituted by at least one —OH, —COOH, —C(O)O—$C_{1-4}$ alkyl, —C(O)N$(R_2)_2$, or $C_{1-5}$ cycloalkyl;

or a pharmaceutically acceptable salt form thereof.

24. The compound of claim 23, having a structure of Formula (IA):

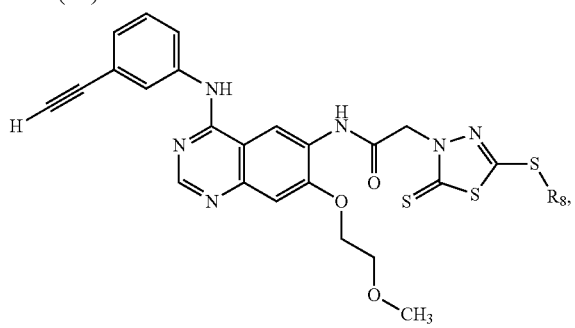

-continued

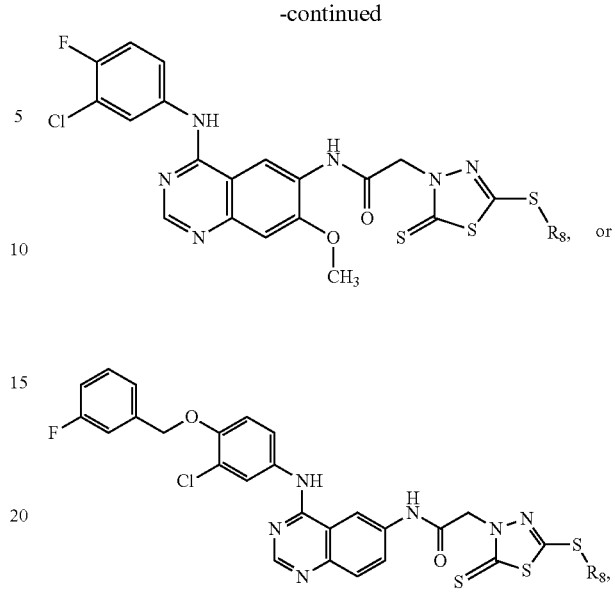

or a pharmaceutically acceptable salt form thereof.

25. A pharmaceutical composition comprising a compound of claim 23 and a pharmaceutically acceptable excipient, suitable for administration to a human patient.

26. The compound of claim 23, having a structure:

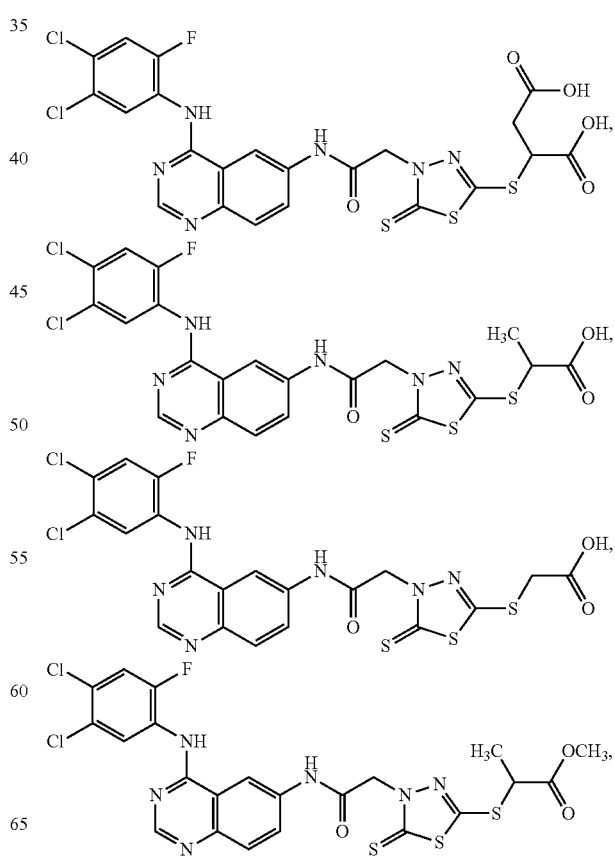

-continued

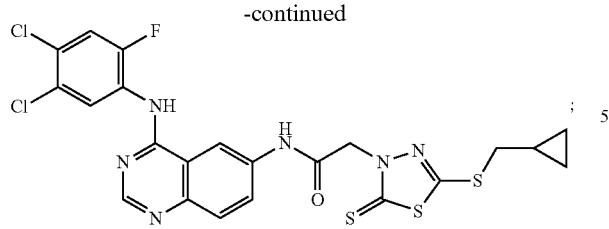

or a pharmaceutically acceptable salt thereof.

27. The compound of claim 1, wherein each $R_1$ is independently H, optionally substituted $C_{2-6}$ alkynyl, optionally substituted benzyloxy, or halo.

28. The compound of claim 23, wherein each $R_1$ is independently H, optionally substituted C2-6 alkynyl, optionally substituted benzyloxy, or halo.

29. The compound of claim 1, wherein each $R_1$ is independently Cl or F.

30. The compound of claim 23, wherein each $R_1$ is independently Cl or F.

31. The compound of claim 1, wherein $R_2$ is H.

32. The compound of claim 23, wherein $R_2$ is H.

33. The compound of claim 1, wherein $R_4$ is H.

34. The compound of claim 23, wherein $R_4$ is H.

35. The compound of claim 1, wherein X is S.

* * * * *